(12) United States Patent
Imazeki et al.

(10) Patent No.: US 8,669,375 B2
(45) Date of Patent: Mar. 11, 2014

(54) PROCESS FOR PRODUCING ESTER COMPOUND

(71) Applicant: Wako Pure Chemical Industries, Ltd., Osaka (JP)

(72) Inventors: Shigeaki Imazeki, Kawagoe (JP); Ryohiko Kinoshita, Kawagoe (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 0 days.

(21) Appl. No.: 13/658,362

(22) Filed: Oct. 23, 2012

(65) Prior Publication Data

US 2013/0066070 A1    Mar. 14, 2013

Related U.S. Application Data

(62) Division of application No. 12/446,535, filed as application No. PCT/JP2007/070576 on Oct. 20, 2007, now Pat. No. 8,318,964.

(30) Foreign Application Priority Data

Oct. 23, 2006 (JP) ................................. 2006-287181

(51) Int. Cl.
*C07D 305/00* (2006.01)
*C07D 307/00* (2006.01)
*C07D 265/32* (2006.01)

(52) U.S. Cl.
USPC .............................. 549/263; 549/429; 544/87

(58) Field of Classification Search
USPC ...................... 549/429, 263; 544/87
See application file for complete search history.

(56) References Cited

U.S. PATENT DOCUMENTS

| | | | |
|---|---|---|---|
| 3,071,604 A | 1/1963 | Mohan et al. | |
| 4,053,504 A | 10/1977 | Rosenkranz et al. | |
| 5,679,834 A * | 10/1997 | Nishikawa et al. | 560/221 |
| 6,265,495 B1 | 7/2001 | Hirata et al. | |

FOREIGN PATENT DOCUMENTS

| | | |
|---|---|---|
| JP | 4-502466 | 5/1992 |
| JP | 7-188111 | 7/1995 |
| JP | 2001-48838 | 2/2001 |
| JP | 2002-302491 | 10/2002 |
| JP | 2002-302491 | 2/2011 |
| WO | 90/07485 | 7/1990 |

OTHER PUBLICATIONS

Oohashi et al., Efficent Method for the Lactonization of w-hydroxycarboxylic acids with Di-2-thienyl Carbonate by the Promotion of Catalytic amounts of DMAP and Hf(OTf)4 , Chemistry Letters, vol. 34, No. 5, 2005, p. 710-711.

Tatsumi et al., Selective Macrolactonization Using Zeolite Molecular Sieves, J. Chem. Soc., Chem, Commun., 1993, p. 1264-1265.

International Search Report of PCT/JP2007/070576, dated Nov. 13, 2007.

The Chemical Society of Japan. *New Experimental Chemistry course 14 (Shin Jikken Kagaka Kouza) Synthesis and reaction of organic compound II* "I. Carboxylic acids and its derivative, 1.2 Esters, Experimental examples 1.30 and 1.31." Dec. 20, 1977, 3 pages.

Eicher "Seminar Yuki Gosei (Jikken Manual)" $3^{rd}$ ed. Nov. 10, 1989, pp. 117-122.

Karo. "Kan'noki-betsu Yuki Kagobutsn Goseiho [I]" Mar. 25, 1976, pp. 263-265.

* cited by examiner

*Primary Examiner* — Taylor Victor Oh

(74) *Attorney, Agent, or Firm* — Hamre, Schumann, Mueller & Larson, P.C.

(57) ABSTRACT

PROBLEM

To provide an environmentally-friendly method for producing industrially an ester compound.

SOLUTION

The present invention is a method for producing an ester compound which comprises subjecting a carboxylic acid and an alcohol to dehydration-condensation reaction using an involatile acid catalyst and then removing the residual acid catalyst by bringing a weak basic substance into contact with the residual acid catalyst.

19 Claims, No Drawings

PROCESS FOR PRODUCING ESTER COMPOUND

TECHNICAL FIELD

The present invention relates to an environmentally-friendly industrial method for producing an ester compound.

BACKGROUND ART

Researches on an environmentally-friendly chemical process have been lately prevalent and many reports relating to the researches on important esterification reaction that is valuable in use are presented.

The dehydration-condensation reaction of a carboxylic acid and an alcohol using an acid catalyst is known as the most general method for producing an ester compound and specifically includes, for example, (1) a method comprising adding concentrated sulfuric acid (acid catalyst) to a solution of a carboxylic acid and methanol in dichloroethane followed by heating and refluxing, then separating an organic layer by diluting with water, and neutralizing the obtained organic layer with a saturated aqueous solution of sodium hydrogencarbonate and then distilling off the solvent to obtain an ester (Non-patent Literature 1; Experimental Chemistry Course (Jikken Kagaku Kouza), 1. Carboxylic acid and its derivative, 1.2 Esters, page 44, Experimental example 1.30) and (2) a method comprising adding concentrated sulfuric acid (acid catalyst) to a mixture of benzoic acid and anhydrous ethanol followed by heating and refluxing, then distilling off the unreacted alcohol under atmospheric pressure, and adding water of an amount of 5 times, and then neutralizing with solid sodium carbonate, and then extracting the separated oily material with ether, and washing the obtained ether layer with water and distilling off the ether to obtain an ester (Non-patent Literature 1; Experimental example 1.31), etc.

However, in case these methods is used as producing industrially an ester compound, it has not been satisfactory from the standpoint of green chemistry because these methods have the problem that a large amount of water is used for an extraction treatment to an organic layer and neutralization treatment for removing an acid catalyst (for example, a saturated aqueous solution of sodium hydrogencarbonate, and sodium carbonate and water) resulting in a large amount of waste water.

Under these conditions, development of a method for producing industrially an ester compound taking economic efficiency and environment into consideration has been desired.

[Non-patent Literature 1] "New Experimental Chemistry Course 14 (Shin Jikken Kagaku Kouza) Synthesis and reaction of organic compound II" edited by Corporation: The Chemical Society of Japan, published by MARUZEN CO., LTD, Dec. 20, 1977, 1. Carboxylic acid and its derivative, 1.2 Esters, page 44, Experimental examples 1.30 and 1.31)

DISCLOSURE OF INVENTION

Problem to be Solved by the Invention

Considering the above situations, it is an object of the present invention to provide an environmentally-friendly industrial method for producing an ester compound.

Means for Solving the Problem

The present invention is an invention of a method for producing an ester compound which comprises subjecting a carboxylic acid and an alcohol to dehydration-condensation reaction using an involatile acid catalyst and then removing the residual acid catalyst by bringing a weak basic substance into contact with the residual acid catalyst, more specifically a method which comprises subjecting an alcohol represented by a general formula [1]:

$$R^1\text{—OH} \quad [1]$$

(wherein $R^1$ represents an alkyl group having 1 to 18 carbon atoms, an oxygen-atom-containing alkyl group, an alkenyl group, an alkynyl group, an aryl group, an aralkyl group or a heterocyclic group, which may have a substituent)
and a carboxylic acid represented by a general formula [2]:

$$R^2\text{—COOH} \quad [2]$$

(wherein $R^2$ represents an alkyl group having 1 to 18 carbon atoms, an oxygen-atom-containing alkyl group, an alkenyl group, an alkinyl group, an aryl group, an aralkyl group or a heterocyclic group, which may have a substituent) to reaction without any solvent or in a nonaqueous solvent in the coexistence of an involatile acid catalyst and then adding the obtained reaction solution with a weak basic substance followed by removing the formed salt of the weak basic substance and the acid catalyst in the reaction solution to produce an ester compound represented by a general formula [3]:

$$R^1\text{—OCO—}R^2 \quad [3]$$

(wherein $R^1$ and $R^2$ are the same as the above).

Effects of the Invention

The method for producing an ester compound of the present invention can easily remove an acid catalyst in a reaction solution, without the problems accompanied with conventional methods that many steps are necessary for extraction, and that a large amount of water for neutralizing the acid catalyst in a water phase is uneconomical and makes a large volume of waste water, because the neutralization treatment of the acid catalysit is carried out by forming a salt with a weak basic substance and removing the salt thereof, and thus the method of the invention can industrially produce an ester compound in an efficient and environmentally-friendly manner.

BEST MODE FOR CARRYING OUT THE INVENTION

The method for producing an ester compound of the present invention includes, for example, a method for producing an ester compound which comprises subjecting a carboxylic acid and an alcohol to dehydration-condensation reaction using an involatile acid catalyst and then removing the residual acid catalyst by bringing a weak basic substance into contact with the residual acid catalyst, or more specifically, for example, a method for producing an ester compound which comprises subjecting an alcohol represented by a general formula [1]:

$$R^1\text{—OH} \quad [1]$$

(wherein $R^1$ represents an alkyl group having 1 to 18 carbon atoms, an oxygen-atom-containing alkyl group, an alkenyl group, an alkynyl group, an aryl group, an aralkyl group or a heterocyclic group, which may have a substituent)
and a carboxylic acid represented by a general formula [2]:

$$R^2\text{—COOH} \quad [2]$$

(wherein $R^2$ represents an alkyl group having 1 to 18 carbon atoms, an oxygen-atom-containing alkyl group, an alkenyl group, an alkynyl group, an aryl group, an aralkyl group or a heterocyclic group, which may have a substituent) to reaction without any solvent or in a nonaqueous solvent in the coexistence of an involatile acid catalyst and then adding the obtained reaction solution with a weak basic substance followed by removing the formed salt of the weak basic substance and the acid catalyst in the reaction solution to produce an ester compound represented by a general formula [3]:

$$R^1\text{—OCO—}R^2 \qquad [3]$$

(wherein $R^1$ and $R^2$ are the same as the above).

That is, the alcohol and the carboxylic acid relating to the present invention are not particularly limited as long as they are able to attain the purpose of the present invention. The alcohol includes, for example, an alcohol represented by the above general formula [1] and an alcohol represented by a general formula [9]:

$$\text{HO-}(T_1\text{-O})_n\text{—H} \qquad [9]$$

(wherein $T_1$ represents an alkylene chain having 1 to 4 carbon atoms; and n represents an integer of 1 to 5). The carboxylic acid includes, for example, a carboxylic acid represented by the above general formula [2] and a carboxylic acid represented by a general formula [11]:

$$\text{HOOC-}T_2\text{-COOH} \qquad [11]$$

(wherein $T_2$ represents an alkylene group having 1 to 8 carbon atoms which may have a substituent or an arylene group).

In addition, the alcohol and the carboxylic acid related to the present invention also include a compound having a hydroxyl group and a carboxyl group in the same compound and specifically a compound represented by a general formula [7]:

[7]

(wherein T represents an alkylene chain which may have a substituent)

In the general formulae [1] to [3], the alkyl group of an alkyl group having 1 to 18 carbon atoms which may have a substituent represented by $R^1$ and $R^2$ includes any of a straight-chained, branched and cyclic group, and usually includes a group having 1 to 18 carbon atoms, preferably 1 to 8 carbon atoms and specifically, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 1-methylpentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a n-tridecyl group, an isotridecyl group, a sec-tridecyl group, a tert-tridecyl group, a neotridecyl group, a n-tetradecyl group, an isotetradecyl group, a sec-tetradecyl group, a tert-tetradecyl group, a neotetradecyl group, a n-pentadecyl group, an isopentadecyl group, a sec-pentadecyl group, a tert-pentadecyl group, a neopentadecyl group, a n-hexadecyl group, an isohexadecyl group, a sec-hexadecyl group, a tert-hexadecyl group, a neohexadecyl group, a n-heptadecyl group, an isoheptadecyl group, a sec-heptadecyl group, a tert-heptadecyl group, a neoheptadecyl group, a n-octadecyl group, an isooctadecyl group, a sec-octadecyl group, a tert-octadecyl group, a neooctadecyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, a cyclotridecyl group, a cyclotetradecyl group, a cyclopentadecyl group, a cyclohexadecyl group, a cycloheptadecyl group and a cyclooctadecyl group etc.

The alkenyl group of an alkenyl group which may have a substituent represented by $R^1$ and $R^2$ includes any of a straight-chained, branched and cyclic group, and usually includes a group having 2 to 12, preferably 2 to 8 carbon atoms and specifically, for example, a vinyl group, an allyl group, a 1-propenyl group, an isopropenyl group, a 1-butenyl group, a 2-butenyl group, a 3-butenyl group, a 2-methylallyl group, a 1-pentenyl group, a 2-pentenyl group, a 3-pentenyl group, a 4-pentenyl group, a 2-methyl-2-butenyl group, a 1-hexenyl group, a 2-hexenyl group, a 3-hexenyl group, a 5-hexenyl group, a 2-methyl-2-pentenyl group, a 1-heptenyl group, a 2-heptenyl group, a 3-heptenyl group, a 4-heptenyl group, a 5-heptenyl group, a 6-heptenyl group, a 1-octenyl group, a 2-octenyl group, a 3-octenyl group, a 4-octenyl group, a 1-nonenyl group, a 2-nonenyl group, a 3-nonenyl group, a 4-nonenyl group, a 1-decenyl group, a 2-decenyl group, a 3-decenyl group, 4-decenyl group, a 5-decenyl group, a 1-undecenyl group, a 2-undecenyl group, a 3-undecenyl group, a 4-undecenyl group, a 5-undecenyl group, a 1-dodecenyl group, a 2-dodecenyl group, a 3-dodecenyl group, a 4-dodecenyl group, a 5-dodecenyl group, a 6-dodecenyl group, a 1-cyclobutenyl group, a 1-cyclopentenyl group and a 1-cyclohexenyl group etc.

The alkynyl group of an alkynyl group which may have a substituent represented by $R^1$ and $R^2$ includes any of a straight-chained, branched and cyclic group, and usually includes a group having 2 to 12 carbon atoms, preferably 2 to 8 carbon atoms and specifically, for example, an ethenyl group, a 2-propynyl group, a 2-pentynyl group, a 2-nonyl-3-butynyl group, a cyclohexyl-3-ynyl group, a 4-octynyl group and a 1-methyldecyl-5-ynyl etc.

The aryl group of an aryl group which may have a substituent represented by $R^1$ and $R^2$ usually includes a group having 6 to 18 carbon atoms and specifically, for example, a phenyl group, a naphthyl group, an anthryl group, a phenanthryl group and a naphthacenyl group etc.

The aralkyl group of an aralkyl group which may have a substituent represented by $R^1$ and $R^2$ usually includes a group having 7 to 15 carbon atoms and specifically, for example, a benzyl group, a phenetyl group, a phenylpropyl group, a naphthylmethyl group and a biphenyl group etc.

The heterocyclic group of a heterocyclic group which may have a substituent represented by $R^1$ and $R^2$ includes, for example, a 5-membered ring or a 6-membered ring, that contains 1 to 3 hetero atoms such as, for example, a nitrogen atom, an oxygen atom and a sulfur atom and specifically, includes an aliphatic heterocyclic group such as, for example, a pyrrolidyl-2-one group, a piperidyl group, a piperidino group, a piperazinyl group and a morpholino group and an aromatic heterocyclic group such as, for example, a pyridyl group, an imidazolyl group, a thiazolyl group, a furyl group and a pyranyl group etc.

The oxygen-atom-containing alkyl group which may have a substituent represented by $R^1$ and $R^2$ includes a group having 1 to 5 oxygen atoms in the chain of an alkyl group which may have a substituent and specifically, for example, includes a group represented by a general formula [13]:

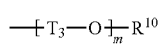
[13]

(wherein $R^{10}$ represents an alkyl group which may have a substituent; m pieces of $T_3$ s indicate each independently an alkylene chain of 1 to 4 carbon atoms which may have a substituent; and m represents an integer of 1 to 6).

In the general formula [13], the alkyl group of an alkyl group which may have a substituent represented by $R^{10}$ includes any of a straight-chained, branched and cyclic group, and usually includes a group having 1 to 12 carbon atoms, preferably 1 to 6 carbon atoms and specifically, for example, the similar one to the exemplification of 1 to 12 carbon atoms of the alkyl groups having 1 to 18 carbon atoms which may have a substituent represented by $R^1$ and $R^2$.

The alkylene chain having 1 to 4 carbon atoms which may have a substituent represented by $T_3$ usually includes a straight-chained alkylene group having 1 to 4 carbon atom, preferably 2 to 3 carbon atoms and specifically, for example, a methylene group, an ethylene group, a trimethylene group and a tetramethylene group etc.

In the general formula [1], the substituent of the alkyl group, alkenyl group or alkinyl group, which has a substituent, represented by $R^1$ includes, for example, a halogen atom, a haloalkyl group, an alkoxy group, a haloalkoxy group, a thioalkoxy group, an acyl group, a substituted amino group, a hydroxyl group, a cyano group, a carboxyl group, a nitrile group and a nitro group etc.

The substituent of the aryl group, aralkyl group or heterocyclic group, which has a substituent, represented by $R^1$ includes, for example, a halogen atom, an alkyl group, a haloalkyl group, an alkenyl group, an alkoxy group, a haloalkoxy group, a thioalkoxy group, an acyl group, a substituted amino group, a hydroxyl group, a cyano group, a carboxyl group, a nitrile group and a nitro group etc.

In the general formula [2], the substituent of the alkyl group or alkenyl group, which has a substituent, represented by $R^2$ includes, for example, a halogen atom, a haloalkyl group, an alkoxy group, a haloalkoxy group, a thioalkoxy group, an acyl group, a substituted amino group, a carboxyl group, a cyano group, a nitrile group and a nitro group etc.

The substituent of the aryl group, aralkyl group or heterocyclic group, which has a substituent, represented by $R^2$ includes, for example, a halogen atom, an alkyl group, a haloalkyl group, an alkenyl group, an alkoxy group, a haloalkoxy group, a thioalkoxy group, an acyl group, a substituted amino group, a hydroxyl group, a cyano group, a carboxyl group, a nitrile group and a nitro group etc.

The halogen atom as a substituent includes, for example, includes a fluorine atom, a chlorine atom, a bromine atom and an iodine atom.

The haloalkyl group as a substituent includes any of a straight-chained, branched and cyclic group, and usually includes a group wherein a part or all of the hydrogen atoms in an alkyl group having of 1 to 18 carbon atoms, preferably 1 to 6 carbon atoms are substituted with a halogen atom (For example, a fluorine atom, a bromine atom, a chlorine atom and an iodine atom etc. are included and a fluorine atom is preferable among these.) and specifically, for example, a fluoromethyl group, a chloromethyl group, a bromomethyl group, an iodomethyl group, a trifluoromethyl group, a trichloromethyl group, a tribromomethyl group, a 2-fluoroethyl group, a 2-chloroethyl group, a 2-bromoethyl group, a pentaiodoethyl group, a pentachloroethyl group, a pentafluoroethyl group, a pentabromoethyl group, a 3-fluoropropyl group, a 3-chloropropyl group, a 3-bromopropyl group, a trifluoropropyl group, a trichloropropyl group, a tribromopropyl group, a di(trifluoromethyl)methyl group, a di(trichloromethyl)methyl group, a di(tribromomethyl)methyl group, a heptafluoropropyl group, a heptachloropropyl group, a 4-fluorobutyl group, a 4-chlorobutyl group, a 4-bromobutyl group, a nonafluorobutyl group, a nonachlorobutyl group, a nonaburomobutyl group, a 5-fluoropentyl group, a 5-chloropentyl group, a 5-bromopentyl group, a 2,2,3,3,4,4,5,5-octafluoropentyl group ($—CH_2(CF_2)_4H$), a 2,2,3,3,4,4,5,5-octachloropentyl group ($—CH_2(CCl_2)_4H$), a 2,2,3,3,4,4,5,5-octabromopentyl group ($—CH_2(CBr_2)_4H$), a perfluoropentyl group, a perchloropentyl group, a perbromopentyl group, a 6-fluorohexyl group, a 6-chlorohexyl group, a 6-bromohexyl group, a perfluorohexyl group, a perchlorohexyl group, a perbromohexyl group, a perfluoroheptyl group, a perchloroheptyl group, a perbromoheptyl group, a perfluorooctyl group, a perchlorooctyl group, a perbromooctyl group, a perfluorononyl group, a perchlorononyl group, a perbromononyl group, a 3,3,4,4,5,5,6,6,7,7,8,8,9,9,10,10,10-heptadecafluorodecyl group ($—(CH_2)_2(CF_2)_7CF_3$), a 3,3,4,4,5,5,6,6,7,7,8,8,9,9,10,10,10-heptadecachlorodecyl group ($—(CH_2)_2(CCl_2)_7CBr_3$), a 3,3,4,4,5,5,6,6,7,7,8,8,9,9,10,10,10-heptadecabromodecyl group ($—(CH_2)_2(CBr_2)_7CBr_3$), a perfluorodecyl group, a perchlorodecyl group, a perbromodecyl group, a perfluoroundecyl group, a perchloroundecyl group, a perbromoundecyl group, perfluorododecyl group, a perchlorododecyl group, a perbromododecyl group, a perfluorotridecyl group, a perchlorotridecyl group, a perbromotridecyl group, a perfluorotetradecyl group, a perchlorotetradecyl group, a perbromotetradecyl group, a perfluoropentadecyl group, a perchloropentadecyl group, a perbromopentadecyl group, a perfluorohexadecyl group, a perchlorohexadecyl group, a perbromohexadecyl group, a perfluoroheptadecyl group, a perchloroheptadecyl group, a perbromoheptadecyl group, a perfluorooctadecyl group, a perchlorooctadecyl group and a perbromooctadecyl group etc.

The alkoxy group as a substituent includes any of a straight-chained, branched and cyclic group, and usually includes a group having 1 to 18 carbon atoms, preferably 1 to 8 carbon atoms and specifically, for example, a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a tert-pentyloxy group, a neopentyloxy group, a n-hexyloxy group, an isohexyloxy group, a sec-hexyloxy group, a tert-hexyloxy group, a neohexyloxy group, a n-heptyloxy group, an isoheptyloxy group, a sec-heptyloxy group, a tert-heptyloxy group, a neoheptyloxy group, a n-octyloxy group, an isooctyloxy group, a sec-octyloxy group, a tert-octyloxy group, a neooctyloxy group, a n-nonyloxy group, an isononyloxy group, a sec-nonyloxy group, a tert-nonyloxy group, a neononyloxy group, a n-decyloxy group, an isodecyloxy group, a sec-decyloxy group, a tert-decyloxy group, a neodecyloxy group, a n-undecyloxy group, an isoundecyloxy group, a sec-undecyloxy group, a tert-undecyloxy group, a neoundecyloxy group, a n-dodecyloxy group, an isododecyloxy group, a sec-dodecyloxy group, a tert-dodecyloxy group, a neododecyloxy group, a n-tridecyloxy group, an isotridecyloxy group, a sec-tridecyloxy group, a tert-tridecyloxy group, a neotridecyloxy group, a n-tetradecyloxy group, an isoteteradecyloxy group, a sec-tetradecyloxy group, a tert-tetradecyloxy group, a neotetradecyloxy group, a n-pentadecyloxy group, an isopentadecyloxy group, a sec-pentadecyloxy group, a tert-pentadecyloxy group, a neopentadecyloxy group, a n-hexadecyloxy group, an isohexadecyloxy group, a sec-hexadecyloxy group, a tert-hexadecyloxy group, a neohexadecyloxy group, a n-heptadecyloxy group, an isoheptadecyloxy group, a sec-heptadecyloxy group, a tert-heptadecyloxy group, a neoheptadecyloxy group, a n-octadecyloxy group, an isooctadecyloxy group, a sec-octadecyloxy group, a tert-octadecyloxy group, an neooctadecyloxy group, a cyclopropoxy group, a cyclobutyloxy group, a cyclopentyloxy group, a cyclohexyloxy group, a cycloheptyloxy group, a cyclooctyloxy group, a cyclononyloxy group, a cyclodecyloxy group, a cycloundecyloxy group, a cyclododecyloxy group, a cyclotridecyloxy group, a cyclotetradecyloxy group, a cyclopentadecyloxy group, a cyclohexadecyloxy group, a cycloheptadecyloxy group and a cyclooctadecyloxy group etc.

The haloalkoxy group as a substituent includes any of a straight-chained, branched and cyclic group, and usually includes a group wherein a part or all of the hydrogen atoms of an alkoxy group of 1 to 18, preferably 1 to 8 carbon atoms are substituted with a halogen atom (For example, a fluorine atom, a bromine atom, a chlorine atom and an iodine atom are included and a fluorine atom is preferable among these.) and specifically, for example, a fluoromethoxy group, a chloromethoxy group, a bromomethoxy group, an iodomethoxy group, a trifluoromethoxy group, a trichloromethoxy group, a tribromomethoxy group, a 2-fluoroethoxy group, a 2-chloroethoxy group, a 2-bromoethoxy group, a pentaiodoethoxy group, a pentachloroethoxy group, a pentafluoroethoxy group, a pentabromoethoxy group, a 3-fluoropropoxy group, a 3-chloropropoxy group, a 3-bromopropoxy group, a trifluoropropoxy group, a trichloropropoxy group, a tribromopropoxy group, a di(trifluoromethyl)methoxy group, a di(trichloromethyl)methoxy group, a di(tribromomethyl)methoxy group, a heptafluoropropoxy group, a heptachloropropoxy group, a 4-fluorobutoxy group, a 4-chlorobutoxy group, a 4-bromobutoxy group, a nonafluorobutoxy group, a nonachlorobutoxy group, a nonabromobutoxy group, a 5-fluoropentyloxy group, a 5-chloropentyloxy group, a 5-bromopentyloxy group, a perfluoropentyloxy group, a perchloropentyloxy group, a perbromopentyloxy group, a 6-fluorohexyloxy group, a 6-chlorohexyloxy group, a 6-bromohexyloxy group, a perfluorohexyloxy group, a perchlorohexyloxy group, a perbromohexyloxy group, a perfluoroheptyloxy group, a perchloroheptyloxy group, a perbromoheptyloxy group, a perfluorooctyloxy group, a perchlorooctyloxy group, a perbromooctyloxy group, a perfluorononyloxy group, a perchlorononyloxy group, a perbromononyloxy group, a perfluorodecyloxy group, a perchlorodecyloxy group, a perbromodecyloxy group, a perfluoroundecyloxy group, a perchloroundecyloxy group, a perbromoundecyloxy group, a perfluorododecyloxy group, a perchlorododecyloxy group, a perbromododecyloxy group, a perfluorotridecyloxy group, a perchlorotridecyloxy group, a perbromotridecyloxy group, a perfluorotetradecyloxy group, a perchlorotetradecyloxy group, a perbromotetradecyloxy group, a perfluoropentadecyloxy group, a perchloropentadecyloxy group, a perbromopentadecyloxy group, a perfluorohexadecyloxy group, a perchlorohexadecyloxy group, a perbromohexadecyloxy group, a perfluoroheptadecyloxy group, a perchloroheptadecyloxy group, a perbromoheptadecyloxy group, a perfluorooctadecyloxy group, a perchlorooctadecyloxy group and a perbromooctadecyloxy group etc.

The thioalkoxy group as a substituent includes any of a straight-chained, branched and cyclic group, and usually includes a group wherein the oxygen atom of an alkoxy group having 1 to 18 carbon atoms, preferably 1 to 8 carbon atoms is substituted with a sulfur atom and specifically, for example, a methylthio group, an ethylthio group, a n-propylthio group, an isopropylthio group, a n-butylthio group, an isobutylthio group, a sec-butylthio group, a tert-butylthio group, a n-pentylthio group, an isopentylthio group, a sec-pentylthio group, a tert-pentylthio group, a neopentylthio group, a 1-methylpentylthio group, a n-hexylthio group, an isohexylthio group, a sec-hexylthio group, a tert-hexylthio group, a neohexylthio group, a n-heptylthio group, an isoheptylthio group, a sec-heptylthio group, a tert-heptylthio group, a neoheptylthio group, a n-octylthio group, an isooctylthio group, a sec-octylthio group, a tert-octylthio group, a neooctylthio group, a n-nonylthio group, an isononylthio group, a sec-nonylthio group, a tert-nonylthio group, a neononylthio group, a n-decylthio group, an isodecylthio group, a sec-decylthio group, a tert-decylthio group, a neodecylthio group, a n-undecylthio group, an isoundecylthio group, a sec-undecylthio group, a tert-undecylthio group, a neoundecylthio group, a n-dodecylthio group, an isododecylthio group, a sec-dodecylthio group, a tert-dodecylthio group, a n-tridecylthio group, an isotridecylthio group, a sec-tridecylthio group, a tert-tridecylthio group, a neotridecylthio group, a n-tetradecylthio group, an isoteteradecylthio group, a sec-tetradecylthio group, a tert-tetradecylthio group, a neotetradecylthio group, a n-pentadecylthio group, an isopentadecylthio group, a sec-pentadecylthio group, a tert-pentadecylthio group, a neopentadecylthio group, a n-hexadecylthio group, an isohexadecylthio group, a sec-hexadecylthio group, a tert-hexadecylthio group, a neohexadecylthio group, n-heptadecylthio group, an isoheptadecylthio group, a sec-heptadecylthio group, a tert-heptadecylthio group, a neoheptadecylthio group, a n-octadecylthio group, an isooctadecylthio group, a sec-octadecylthio group, a tert-octadecylthio group, a neooctadecylthio group, a cyclopropylthio group, a cyclobutylthio group, a cyclopentylthio group, a cyclohexylthio group, a cycloheptylthio group, a cyclooctylthio group, a cyclononylthio group, a cyclodecylthio group, a cycloundecylthio group, a cyclododecylthio group, a cyclotridecylthio group, a cyclotetradecylthio group, a cyclopentadecylthio group, a cyclohexadecylthio group, a cycloheptadecylthio group and a cyclooctadecylthio group etc.

The acyl group as a substituent usually includes a group derived from a carboxylic acid having 1 to 20 carbon atoms and specifically, for example, a group derived from an aliphatic carboxylic acid such as, for example, a formyl group, an acetyl group, a propionyl group, a butyryl group, an isobutyryl group, a valeryl group, an isovaleryl group, a pivaloyl group, a hexanoyl group, a heptanoyl group, an octanoyl group, a nonanoyl group, a decanoyl group, a dodecanoyl group, a tridecanoyl group, a tetradecanoyl group, a pentadecanoyl group, a hexadecanoyl group, a heptadecanoyl group, an octadecanoyl group, a nonadecanoyl group and an icosanoyl group, and for example, a group derived from an aromatic carboxylic acid such as, for example, a benzoyl group and a naphthoyl group etc.

The substituted amino group as a substituent includes a group wherein 2 hydrogen atoms in an amino group are substituted with, for example, an alkyl group having 1 to 6 carbon atoms or an aryl group etc.

The alkyl group of 1 to 10 carbon atoms as a substituent of the substituted amino group includes any of a straight-chained, branched and cyclic group and specifically, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 1-methylpentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a cyclopropyl group, a cyclobutyl group, a cyclopentyl group, a cyclohexyl group, a cycloheptyl group, a cyclooctyl group, a cyclononyl group, a cyclodecyl group and an adamantyl group etc.

The aryl group as a substituent of the substituted amino group usually includes a group having 6 to 14 carbon atoms, preferably 6 to 10 carbon atoms and specifically, for example, a phenyl group, a naphthyl group, a phenanthryl group and an anthryl group etc.

The alkyl group as a substituent includes any of a straight-chained, branched and cyclic group, and usually includes a group of 1 to 18 carbon atoms and specifically, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 1-methylpentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a n-tridecyl group, an isotridecyl group, a sec-tridecyl group, a tert-tridecyl group, a neotridecyl group, a n-tetradecyl group, an isotetradecyl group, a sec-tetradecyl group, a tert-tetradecyl group, a neotetradecyl group, a n-pentadecyl group, an isopentadecyl group, a sec-pentadecyl group, a tert-pentadecyl group, a neopentadecyl group, a n-hexadecyl group, an isohexadecyl group, a sec-hexadecyl group, a tert-hexadecyl group, a neohexadecyl group, a n-heptadecyl group, an isoheptadecyl group, a sec-heptadecyl group, a tert-heptadecyl group, a neoheptadecyl group, a n-octadecyl group, an isooctadecyl group, a sec-octadecyl group, a tert-octadecyl group, a neooctadecyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, a cyclotridecyl group, a cyclotetradecyl group, a cyclopentadecyl group, a cyclohexadecyl group, a cycloheptadecyl group and a cyclooctadecyl group etc.

The alkenyl group as a substituent includes any of a straight-chained, branched and cyclic group, and usually includes a group having 2 to 12 carbon atoms, preferably 2 to 8 carbon atoms and specifically, for example, a vinyl group, an allyl group, a 1-propenyl group, an isopropenyl group, a 1-butenyl group, a 2-butenyl group, a 3-butenyl group, a 2-methylallyl group, a 1-pentenyl group, a 2-pentenyl group, a 3-pentenyl group, a 4-pentenyl group, a 2-methyl-2-butenyl group, a 1-hexenyl group, a 2-hexenyl group, a 3-hexenyl group, a 5-hexenyl group, a 2-methyl-2-pentenyl group, a 1-heptenyl group, a 2-heptenyl group, a 3-heptenyl group, a 4-heptenyl group, a 5-heptenyl group, a 6-heptenyl group, a 1-octenyl group, a 2-octenyl group, a 3-octenyl group, a 4-octenyl group, a 1-nonenyl group, a 2-nonenyl group, a 3-nonenyl group, a 4-nonenyl group, a 1-decenyl group, a 2-decenyl group, a 3-decenyl group, a 4-decenyl group, a 5-decenyl group, a 1-undecenyl group, a 2-undecenyl group, a 3-undecenyl group, a 4-undecenyl group, a 5-undecenyl group, a 1-dodecenyl group, a 2-dodecenyl group, a 3-dodecenyl group, a 4-dodecenyl group, a 5-dodecenyl group, a 6-dodecenyl group, a 1-cyclobutenyl group, a 1-cyclopentenyl group and a 1-cyclohexenyl group etc.

In the general formula [7], the alkylene chain of an alkylene chain which may have a substituent represents a straight-chained alkylene group having usually 2 to 8 carbon atoms, preferably 3 to 6 carbon atoms and includes specifically, for example, an ethylene group, a trimethylene group, a tetramethylene group, a pentamethylene group, a hexamethylene group, a heptamethylene group and an octamethylene group etc.

The substituent of an alkylene chain which may have a substituent is not particularly limited as long as it has no adverse effect on the ester condensation reaction and includes, for example, the similar one to the exemplification of the substituent of the alkyl group, alkenyl group or alkinyl group which has a substituent represented by $R^1$ in the general formula [1].

In the general formula [9], the alkylene chain of 1 to 4 carbon atoms represented by $T_1$ usually includes a straight-chained alkylene group having 1 to 4 carbon atoms, preferably 2 to 3 carbon atoms and specifically, for example, a methylene group, an ethylene group, a trimethylene group and a tetramethylene group etc.

In the general formula [11], the alkylene group of an alkylene group of 1 to 8 carbon atoms which may have a substituent represented by $T_2$ includes a straight-chained or branched, and usually includes a group having 1 to 8 carbon atoms and specifically, for example, a methylene group, an ethylene group, a trimethylene group, a propylene group, a tetramethylene group, a butylene group, a 2-methylpropylene group, a pentamethylene group, a pentylene group, a 2-methyltetramethylene group, a 2,2-dimethyltrimethylene group, a 2-ethyltrimethylene group, a hexamethylene group, a hexylene group, a 2-methylpentamethylene group, a 3-methylpentamethylene group, a heptamethylene group, a heptylene group, an octylene group and a 2-ethylhexylene group etc.

The arylene group of an arylene group which may have a substituent represented by $T_2$ usually includes a group having 6 to 10 carbon atoms and specifically, for example, an o-phenylene group, a m-phenylene group, a p-phenylene group, a 1,5-naphthylene group, a 1,8-naphthylene group, a 2,7-naphthylene group and a 2,6-naphthylene group etc.

The substituent of an alkylene group having 1 to 8 carbon atoms or an arylene group, which may have a substituent, represented by $T_2$ is not particularly limited as long as it has no adverse effect on the ester condensation reaction and includes, for example, the similar one to the exemplification of the substituent of the alkyl group, alkenyl group or alkinyl group, which has a substituent, represented by $R^1$ in the general formula [1].

The corresponding ester compound obtained by the method of the present invention, that is, the condensation reaction of an alcohol and a carboxylic acid includes, for example, the following compounds, That is, (i) a compound represented by the general formula [3]:

$$R^1—OCO—R^2 \quad [3]$$

(wherein $R^1$ and $R^2$ are the same as the above) that is obtained by reacting 1 equivalent of an alcohol represented by the general formula [1] and 1 equivalent of a carboxylic acid represented by the general formula [2];

(ii) a compound represented by the general formula [8]:

[8]

(wherein T is the same as the above) that is obtained from a compound represented by the general formula [7] wherein an alcohol and a carboxylic acid are the same compound;

(iii) a compound represented by the general formula [10]:

$$R^2—COO\text{-}(T_1\text{-}O)_n—OC—R^2 \quad [10]$$

(wherein $R^2$, $T_1$ and n are the same as the above) that is obtained by reacting 1 equivalent of a dialcohol represented by the general formula [9] and 2 equivalents of a carboxylic acid represented by the general formula [2]; and (iv) a compound represented by the general formula [12]:

$$R^1—OCO\text{-}T_2\text{-}COO—R^1 \quad [12]$$

(wherein $R^1$ and $T_2$ are the same as the above) that is obtained by reacting 2 equivalents of an alcohol represented by the general formula [1] and 1 equivalent of a dicarboxylic acid represented by the general formula [11].

The preferable specific example of alcohols represented by the general formula [1] includes saturated aliphatic alcohols such as, for example, methanol, ethanol, n-propanol, isopropanol, n-butanol, 2-butanol, 2-methyl-1-propanol, 2-methyl-2-propanol, tert-butanol, n-pentanol, tert-amyl alcohol, 2-methyl-1-butanol, 3-methyl-1-butanol, 3-methyl-2-butanol, neopentyl alcohol, 2-pentanol, 3-pentanol, 2,3-dimethyl-2-butanol, 3,3-dimethyl-1-butanol, 3,3-dimethyl-2-butanol, 2-ethyl-1-butanol, n-hexanol, 2-hexanol, 3-hexanol, cyclohexanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 2,2-dimethyl-3-pentanol, 2,3-dimethyl-3-pentanol, 2,4-dimethyl-3-pentanol, 4,4-dimethyl-2-pentanol, 3-ethyl-3-pentanol, n-heptanol, 2-heptanol, 3-heptanol, 2-methyl-2-hexanol, 2-methyl-3-hexanol, 5-methyl-1-hexanol, 5-methyl-2-hexanol, 1-cyclohexyl ethanol, 2-cyclohexyl ethanol, n-octanol, 2-ethylhexyl alcohol, 3-cyclopentyl-1-propanol, 2,3-dimethylcyclohexanol, 2,6-dimethylcyclohexanol, 3,5-dimethylcyclohexanol, 2-ethylcyclohexanol, 4-ethylcyclohexanol, 6-methyl-5-heptene-2-ol, 1-octene-3-ol, 2,2-dimethyl-4-heptanol, 3-ethyl-2,2-dimethyl-3-pentanol, 3-methyl-3-octanol, cyclooctanol, n-nonanol, 2-nonanol, 3,5,5-trimethyl-1-hexanol, 2-decanol, n-decanol, 4-decanol, decyl alcohol, 3,7-dimethyl-1-octanol, 3,7-dimethyl-3-octanol, n-undecanol, 2-undecanol, 2-butyl-1-octanol, n-dodecanol, 2-dodecanol, lauryl alcohol and stearyl alcohol; alicyclic alcohols such as, for example, menthol, borneol, cyclohexanol, cyclopentanol and cycloheptanol; halogen-substituted aliphatic alcohols such as, for example, perfluoroethanol, 2-fluoroethanol, 2,2-difluoroethanol, 2,2,2-trifluoroethanol, pentafluoroethanol, 1-chloroethanol, 2,2-dichloroethanol, 2,2,2-trichloroethanol, 2-bromoethanol, 2,2,2-tribromoethanol, 2-iodoethanol, and 3,3,4,4,5, 5,6,6,7,7,8,8,8-tridecafluorooctane-1-ol; formyl-substituted aliphatic alcohols such as, for example, 5-hydroxyhexanol; carboxy-substituted aliphatic alcohols such as, for example, 3-hydroxy-1-cyclohexane carboxylic acid; aromatic alcohols such as, for example, phenol, cresol, 2,3-xylenol, carvacrol, thymol, naphthol, anthrol, phenanthrol and 1-chrysenol; aromatic aliphatic alcohols such as, for example, benzyl alcohol, phenethyl alcohol, triphenylmethanol and 2-naphthalene ethanol; aralkyl alcohols such as, for example, allyl alcohol, geraniol, phytol, 2-ethyl-2-buten-1-ol and 2-cyclohexene-1-ol; unsaturated aliphatic alcohols such as, for example, alkenyl alcohols including, for example, propargyl alcohol; heterocycle-substituted alcohols such as, for example, 8-quinolinol, indole-5-ol, 3-hydroxythiophene, 1-hydroxypiperidine and furfuryl alcohol; and, for example, ethylene glycol monomethyl ether, diethylene glycol monomethyl ether, triethylene glycol monomethyl ether, tetraethylene glycol monomethyl ether, pentaethylene glycol monomethyl ether and hexaethylene glycol monomethyl ether etc.

The preferable specific example of dialcohols represented by the general formula [9] includes, for example, ethylene glycol, diethylene glycol, triethylene glycol, tetraethylene glycol, pentaethylene glycol and hexaethylene glycol etc.

The preferable specific example of carboxylic acids represented by the general formula [2] includes saturated aliphatic carboxylic acids such as, for example, for example, formic acid, acetic acid, propionic acid, butyric acid, isobutyric acid, valeric acid, isovaleric acid, pivalic acid, hexanoic acid, heptanoic acid, octanoic acid, nonanoic acid, decanoic acid, undecanoic acid, lauric acid, tridecanoic acid, myristic acid, pentadecanoic acid, palmitic acid, heptadecanoic acid, stearic acid, nonadecanoic acid, icosanoic acid, henicosanoic acid, docosanoic acid and tricosanoic acid; halogenated saturated aliphatic carboxylic acids such as, for example, fluoroacetic acid, chloroacetic acid, bromoacetic acid, iodoacetic acid, difluoroacetic acid, dichloroacetic acid, dibromoacetic acid, diiodoacetic acid, trifluoroacetic acid, trichloroacetic acid, tribromoacetic acid, triiodoacetic acid, 2-fluoropropionic acid, 2-chloropropionic acid, 2-bromopropionic acid, 2-iodopropionic acid, trifluoropropionic acid, trichloropropionic acid, pentafluoropropionic acid, pentachloropropionic acid, pentabromopropionic acid, pentaiodopropionic acid, 2,2-bis(trifluoromethyl)propionic acid, 2,2-bis(trichloromethyl)propionic acid, 2,2-bis(tribromomethyl)propionic acid, 2,2-bis(triiodomethyl)propionic acid, trifluorobutyric acid, trichlorobutyric acid, pentafluorobutyric acid, heptachlorobutyric acid, heptafluorobutyric acid, heptabromobutyric acid, heptaiodobutyric acid, heptafluoroisobutyric acid, heptachloroisobutyric acid, heptabromoisobutyric acid, heptaiodoisobutyric acid, trifluorovaleric acid, 5H-perfluorovaleric acid, 5H-perchlorovaleric acid, 5H-perbromovaleric acid, 5H-periodovaleric acid, nonafluorovaleric acid, nonachlorovaleric acid, nonabromovaleric acid, nonaiodovaleric acid, trifluorohexanoic acid, trichlorohexanoic acid, perfluorohexanoic acid, perchlorohexanoic acid, perbromohexanoic acid, periodohexanoic acid, 7-chlorododecafluoroheptanoic acid, 7-chlorododecachloroheptanoic acid, 7-chlorododecabromoheptanoic acid, 7-chlorododecaiodoheptanoic acid, trifluoroheptanoic acid, trichloroheptanoic acid, 7H-perfluoroheptanoic acid, 7H-perchloroheptanoic acid, 7H-perbromoheptanoic acid, 7H-periodoheptanoic acid, trifluorooctanoic acid, trichlorooctanoic acid, pentadecafluorooctanoic acid, pentadecachlorooctanoic acid, pentadecabromooctanoic acid, pentadecaiodooctanoic acid, trifluorononanoic acid, trichlorononanoic acid, 9H-hexadecafluorononanoic acid, 9H-hexadecachlorononanoic acid, 9H-hexadecabromononanoic acid, 9H-hexadecaiodononanoic acid, perfluorononanoic acid, perchlorononanoic acid, perbromononanoic acid, periodononanoic acid, trifluorodecanoic acid, trichlorodecanoic acid, nonadecafluorodecanoic acid, nonadecachlorodecanoic acid, nonadecabromodecanoic acid, nonadecaiododecanoic acid, trifluoroundecanoic acid, trichloroundecanoic acid, perfluoroundecanoic acid, perchloroundecanoic acid, perbromoundecanoic acid, periodoundecanoic acid, trifluorododecanoic acid, trichlorododecanoic acid, perfluorododecanoic acid, perchlorododecanoic acid, perbromododecanoic acid, periodododecanoic acid, trifluorotridecanoic acid, trichlorotridecanoic acid, perfluorotridecanoic acid, perchlorotridecanoic acid, perbromotridecanoic acid, periodotridecanoic acid, trifluorotetradecanoic acid, trichlorotetradecanoic acid, perfluorotetradecanoic acid, perchlorotetradecanoic acid, perbromotetradecanoic acid, periodotetradecanoic acid, trifluoropentadecanoic acid, trichloropentadecanoic acid, perfluoropentadecanoic acid, perchloropentadecanoic acid, perbromopentadecanoic acid, periodopentadecanoic acid, perfluorohexadecanoic acid, perchlorohexadecanoic acid, perbromohexadecanoic acid, periodohexadecanoic acid, perfluoroheptadecanoic acid, perchloroheptadecanoic acid, perbromoheptadecanoic acid, periodoheptadecanoic acid, perfluorooctadecanoic acid, perchlorooctadecanoic acid, perbromooctadecanoic acid, periodooctadecanoic acid, perfluorononadecanoic acid, perchlorononadecanoic acid, perbromononadecanoic acid, periodononadecanoic acid, perfluoroicosanoic acid, perchloroicosanoic acid, perbromoicosanoic acid, periodoicosanoic acid, perfluorohenicosanoic acid, perchlorohenicosanoic acid, perbromohenicosanoic acid, periodohenicosanoic acid, perfluorodocosanoic acid, perchlorodocosanoic acid, perbromodocosanoic acid, periododocosanoic acid, perfluorotricosanoic acid, perchlorotricosanoic acid, perbromotricosanoic acid and periodotricosanoic acid; alicyclic carboxylic acids such as, for example, cyclohexanecarboxylic acid, camphoric acid, adamantane carboxylic acid; halogenated alicyclic carboxylic acids such as, for example, 4-fluorocyclohexanecarboxylic acid, 4-chlorocyclohexanecarboxylic acid, 4-bromocyclohexanecarboxylic acid, 4-iodocyclohexanecarboxylic acid, pentafluorocyclohexanecarboxylic acid, pentachlorocyclohexanecarboxylic acid, pentabromocyclohexanecarboxylic acid, pentaiodocyclohexanecarboxylic acid, 4-(trifluoromethyl)cyclohexanecarboxylic acid, 4-(trichloromethyl)cyclohexanecarboxylic acid, 4-(tribromomethyl)cyclohexanecarboxylic acid and 4-(triiodomethyl)cyclohexanecarboxylic acid; alkylthioaliphatic carboxylic acids such as, for example, methylthioacetic acid, ethylthioacetic acid, propylthioacetic acid, isopropylthioacetic acid, butylthioacetic acid, isobutylthioacetic acid, t-butylthioacetic acid and 3-methylthiopropionic acid; alkoxyaliphatic carboxylic acids such as, for example, methoxyacetic acid, ethoxyacetic acid, propoxyacetic acid, isopropoxyacetic acid, butoxyacetic acid, isobutoxyacetic acid, 3-methoxypropionic acid and 3-methoxybutyric acid; aromatic carboxylic acids such as, for example, benzoic acid, naphthoic acid, anthracenecarboxylic acid, pyrenecarboxylic acid, pyrilenecarboxylic acid and pentaphenecarboxylic acid; halogenated aromatic carboxylic acids such as, for example, fluorobenzoic acid, chlorobenzoic acid, bromobenzoic acid, iodobenzoic acid, difluorobenzoic acid, dichlorobenzoic acid, dibromobenzoic acid, diiodobenzoic acid, trifluorobenzoic acid, trichlorobenzoic acid, tribromobenzoic acid, triiodobenzoic acid, tetrafluorobenzoic acid, tetrachlorobenzoic acid, tetrabromobenzoic acid, tetraiodobenzoic acid, pentafluorobenzoic acid, pentachlorobenzoic acid, pentabromobenzoic acid, pentaiodobenzoic acid, fluoronaphthoic acid, chloronaphthoic acid, bromonaphthoic acid, iodonaphthoic acid, perfluoronaphthoic acid, perchloronaphthoic acid, perbromonaphthoic acid, periodonaphthoic acid, fluoroanthracenecarboxylic acid, chloroanthracenecarboxylic acid, bromoanthracenecarboxylic acid, iodoanthracenecarboxylic acid, perfluoroanthracenecarboxylic acid, perchloroanthracenecarboxylic acid, perbromoanthracenecarboxylic acid and periodoanthracenecarboxylic acid; alkyl substituted aromatic carboxylic acids such as, for example, toluic acid (p-tolylacetic acid) and 2,4,6-tri(isopropyl)benzoic acid; haloalkyl substituted aromatic carboxylic acids such as, for example, 2-trifluoromethylbenzoic acid, 2-trichloromethylbenzoic acid, 2-tribromomethylbenzoic acid, 2-triiodomethylbenzoic acid, 3-trifluoromethylbenzoic acid, 3-trichloromethylbenzoic acid, 3-tribromomethylbenzoic acid, 3-triiodomethylbenzoic acid, 4-trifluoromethylbenzoic acid, 4-trichloromethylbenzoic acid, 4-tribromomethylbenzoic acid, 4-triiodomethylbenzoic acid, 2-fluoro-4-(trifluoromethyl)benzoic acid, 2-chloro-4-(trichloromethyl)benzoic acid, 2-bromo-4-(tribromomethyl)benzoic acid, 2,3,4-trifluoro-6-(trifluoromethyl)benzoic acid, 2,3,4-trichloro-6-(trichloromethyl)benzoic acid, 2,3,4-tribromo-6-(tribromomethyl)benzoic acid, 2,3,4-triiodo-6-(triiodomethyl)benzoic acid, 2-iodo-4-(triiodomethyl)benzoic acid, 2,4-bis(trifluoromethyl)benzoic acid, 2,4-bis(trichloromethyl)benzoic acid, 2,4-bis(tribromomethyl)benzoic acid, 2,4-bis(triiodomethyl)benzoic acid, 2,6-bis(trifluoromethyl)benzoic acid, 2,6-bis(trichloromethyl)benzoic acid, 2,6-bis(tribromomethyl)benzoic acid, 2,6-bis(triiodomethyl)benzoic acid, 3,5-bis(trifluoromethyl)benzoic acid, 3,5-bis(trichloromethyl)benzoic acid, 3,5-bis(tribromomethyl)benzoic acid, 3,5-bis(triiodomethyl)benzoic acid, 2,4,6-tris(trifluoromethyl)benzoic acid, 2,4,6-tris(trichloromethyl)benzoic acid, 2,4,6-tris(tribromomethyl)benzoic acid, 2,4,6-tris(triiodomethyl)benzoic acid, 2-chloro-6-fluoro-3-methylbenzoic acid, trifluoromethylnaphthoic acid, trichloromethylnaphthoic acid, tribromomethylnaphthoic acid, triiodomethylnaphthoic acid, bis(trifluoromethyl)naphthoic acid, bis(trichloromethyl)naphthoic acid, bis(tribromomethyl)naphthoic acid, bis(triiodomethyl)naphthoic acid, tris(trifluoromethyl)naphthoic acid, tris(trichloromethyl)naphthoic acid, tris(tribromomethyl)naphthoic acid, tris(triiodomethyl)naphthoic acid, trifluoromethylanthracenecarboxylic acid, trichloromethylanthracenecarboxylic acid, tribromomethylanthracenecarboxylic acid and triiodomethylanthracenecarboxylic acid; haloalkoxy substituted aromatic carboxylic acids such as, for example, 4-trifluoromethoxybenzoic acid, 4-trichloromethoxybenzoic acid, 4-tribromomethoxybenzoic acid, 4-triiodomethoxybenzoic acid, 4-pentafluoroethoxybenzoic acid, 4-pentachloroethoxybenzoic acid, 4-pentabromoethoxybenzoic acid, 4-pentaiodoethoxybenzoic acid, 3,4-bis(trifluoromethoxy)benzoic acid, 3,4-bis(trichloromethoxy)benzoic acid, 3,4-bis(tribromomethoxy)benzoic acid, 3,4-bis(triiodomethoxy)benzoic acid, 2,5-bis(2,2,2-trifluoroethoxy)benzoic acid, 2,5-bis(2,2,2-trichloroethoxy)benzoic acid, 2,5-bis(2,2,2-tribromoethoxy)benzoic acid and 2,5-bis(2,2,2-triiodoethoxy)benzoic acid; nitro substituted aromatic carboxylic acids such as, for example, trinitrobenzoic acid; aromatic aliphatic carboxylic acids such as, for example, α-toluic acid, hydrocinnamic acid, hydroatropic acid, 3-phenylpropionic acid, 4-phenylbutyric acid, 5-phenylpentanoic acid, 6-phenylhexanoic acid, 7-phenylheptanoic acid and 6-(2-naphthyl)hexanoic acid; oxocarboxylic acids such as, for example, 2-formylacetic acid, acetoacetic acid, 3-benzoylpropionic acid, 4-formylbutyric acid, 3-oxovaleric acid, 5-oxovaleric acid, 3,5-dioxovaleric acid, 6-formylhexanecarboxylic acid, 2-oxo-1-cyclohexanecarboxylic acid, 4-(2-oxobutyl)benzoic acid, p-(3- formylpropyl)benzoic acid, 4-formylphenylacetic acid, β-oxocyclohexanepropionic acid and pyruvic acid; heterocyclic carboxylic acids such as, for example, 2-furancarboxylic acid; ethylenically unsaturated carboxylic acids having 3 to 20 carbon atoms such as, for example, acrylic acid, methacrylic acid, vinylacetic acid, allylacetic acid and vinylbenzoic acid; ethylenically unsaturated carboxylic esters such as, for example, methyl methacrylate, ethyl methacrylate, propyl methacrylate, butyl methacrylate, 2-ethylhexyl methacrylate, methyl acrylate, ethyl acrylate, propyl acrylate, butyl acrylate, 2-ethylhexyl acrylate, lauryl methacrylate and stearyl acrylate (These acids may be a salt such as, for example, a salt of an alkaline metal such as, for example, sodium and potassium, and an ammonium salt.)

The preferable specific example of dicarboxylic acids represented by the general formula [11] includes aliphatic dicarboxylic acids such as, for example, malonic acid, succinic acid, glutaric acid and adipic acid; aromatic dicarboxylic acids such as, for example, phthalic acid, isophthalic acid and terephthalic acid etc.

The preferable specific example of compounds represented by the general formula [7] includes, for example, 2-hydroxyacetic acid, 3-hydroxypropionic acid, 4-hydroxybutanoic acid, 5-hydroxypentanoic acid and 6-hydroxycaproic acid etc.

The typical specific example of compounds represented by the general formula [3] includes, for example, 3,3,4,4,5,5,6,6,7,7,8,8,8-tridecafluorooctane 2-methyl-2-propenate ester, ethyl methylthioacetate, ethyl methoxyacetate, ethyl p-tolylacetate, ethyl 2-furancarboxylate, ethyl 5-chlorovalerate, ethyl acetylacetate, butyl acetate and phenyl acetate.

The typical specific example of compounds represented by the general formula [8] includes, for example, 3-oxiranone, 2-oxetanone, dihydro-2-furanone, tetrahidro-2H-pyrane-2-one and ε-caprolactone.

The typical specific example of compounds represented by the general formula [10] includes, for example, 1,2-ethanediyl dimethyl ester, 3-oxo-2,4,7,10-tetraoxa-11-undecanoic acid methyl ester, 2,5,8,11-tetraoxadodecan dicarboxylic acid dimethyl ester and 2,5,8,11,14-pentaoxapentadodecanoic dicarboxylic acid dimethyl ester.

The typical specific example of compounds represented by the general formula [12] includes, for example, butane dicarboxylic acid dimethyl ester, pentane dicarboxylic acid dimethyl ester, hexane dicarboxylic acid dimethyl ester and benzen dicarboxylic acid dimethyl ester.

The involatile acid catalyst includes a solid or a liquid under ordinary temperature and pressure and specifically, for example, sulfuric acid and a sulfonic acid represented by the general formula [4]:

$$R^3\text{—SO}_3H \qquad [4]$$

(wherein $R^3$ represents an alkyl group, an aryl group or an aralkyl group, which may have a substituent).

In the general formula [4], the alkyl group of an alkyl group which may have a substituent represented by $R^3$ includes any of a straight-chained, branched and cyclic group, and usually includes a group having 1 to 18 carbon atoms, preferably 1 to 4 carbon atoms and specifically, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 1-methylpentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a n-tridecyl group, an isotridecyl group, a sec-tridecyl group, a tert-tridecyl group, a neotridecyl group, a n-tetradecyl group, an isotetradecyl group, a sec-tetradecyl group, a tert-tetradecyl group, a neotetradecyl group, a n-pentadecyl group, an isopentadecyl group, a sec-pentadecyl group, a tert-pentadecyl group, a neopentadecyl group, a n-hexadecyl group, an isohexadecyl group, a sec-hexadecyl group, a tert-hexadecyl group, a neohexadecyl group, a n-heptadecyl group, an isoheptadecyl group, a sec-heptadecyl group, a tert-heptadecyl group, a neoheptadecyl group, a n-octadecyl group, an isooctadecyl group, a sec-octadecyl group, a tert-octadecyl group, a neooctadecyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, a cyclotridecyl group, a cyclotetradecyl group, a cyclopentadecyl group, a cyclohexadecyl group, a cycloheptadecyl group and a cyclooctadecyl group etc.

The aryl group of an aryl group which may have a substituent represented by $R^3$ usually includes a group having 6 to 15 carbon atoms and specifically, for example, a phenyl group, a naphthyl group and an anthryl group etc.

The aralkyl group of an aralkyl group which may have a substituent represented by $R^3$ usually includes a group having 7 to 15 carbon atoms and specifically, for example, a benzyl group, a phenethyl group, a phenylpropyl group and a naphthylmethyl group etc.

The substitute of an alkyl group, an aryl group or an aralkyl group. which has a substituent, represented by $R^3$ includes, for example, a halogen atom, an alkyl group and a haloalkyl group etc.

The halogen atom as a substitute includes, for example, a fluorine atom, a chlorine atom, a bromine atom and an iodine atom etc.

The alkyl group as a substitute includes any of a straight-chained, branched and cyclic group, and usually includes a group having 1 to 12 carbon atoms and specifically, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 1-methylpentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group and a cyclododecyl group etc.

The haloalkyl group as a substituent includes any of a straight-chained, branched and cyclic group, and usually includes a group wherein a part or all of the hydrogen atoms of an alkyl group having 1 to 18 carbon atoms, preferably 1 to 6 carbon atoms are substituted with a halogen atom (For example, a fluorine atom, a bromine atom, a chlorine atom and an iodine atom etc. are included and a fluorine atom is preferable among these.) and specifically, for example, a fluoromethyl group, a chloromethyl group, a bromomethyl group, an iodomethyl group, a trifluoromethyl group, a trichloromethyl group, a tribromomethyl group, a 2-fluoroethyl group, a 2-chloroethyl group, a 2-bromoethyl group, a pentaiodoethyl group, a pentachloroethyl group, a pentafluoroethyl group, a pentabromoethyl group, a 3-fluoropropyl group, a 3-chloropropyl group, a 3-bromopropyl group, a trifluoropropyl group, a trichloropropyl group, a tribromopropyl group, a di(trifluoromethyl)methyl group, a di(trichloromethyl)methyl group, a di(tribromomethyl)methyl group, a heptafluoropropyl group, a heptachloropropyl group, a 4-fluorobutyl group, a 4-chlorobutyl group, a 4-bromobutyl group, a nonafluorobutyl group, a nonachlorobutyl group, a nonaburomobutyl group, a 5-fluoropentyl group, a 5-chloropentyl group, a 5-bromopentyl group, a 2,2,3,3,4,4,5,5-octafluoropentyl group (—$CH_2(CF_2)_4H$), a 2,2,3,3,4,4,5,5-octachloropentyl group (—$CH_2(CCl_2)_4H$), a 2,2,3,3,4,4,5,5-octabromopentyl group (—$CH_2(CBr_2)_4H$), a perfluoropentyl group, a perchloropentyl group, a perbromopentyl group, a 6-fluorohexyl group, a 6-chlorohexyl group, a 6-bromohexyl group, a perfluorohexyl group, a perchlorohexyl group, a perbromohexyl group, a perfluoroheptyl group, a perchloroheptyl group, a perbromoheptyl group, a perfluorooctyl group, a perchlorooctyl group, a perbromooctyl group, a perfluorononyl group, a perchlorononyl group, a perbromononyl group, a 3,3,4,4,5,5,6,6,7,7,8,8,9,9,10,10,10-heptadecafluorodecyl group (—$(CH_2)_2(CF_2)_7CF_3$), a 3,3,4,4,5,5,6,6,7,7,8,8,9,9,10,10,10-heptadecachlorodecyl group (—$(CH_2)_2(CCl_2)_7CCl_3$), a 3,3,4,4,5,5,6,6,7,7,8,8,9,9,10,10,10-heptadecabromodecyl group (—$(CH_2)_2(CBr_2)_7CBr_3$), a perfluorodecyl group, a perchlorodecyl group, a perbromodecyl group, a perfluoroundecyl group, a perchloroundecyl group, a perbromoundecyl group, a perfluorododecyl group, a perchlorododecyl group, a perbromododecyl group, a perfluorotridecyl group, a perchlorotridecyl group, a perbromotridecyl group, a perfluorotetradecyl group, a perchlorotetradecyl group, aperbromotetradecyl group, a perfluoropentadecyl group, a perchloropentadecyl group, a perbromopentadecyl group, a perfluorohexadecyl group, a perchlorohexadecyl group, a perbromohexadecyl group, a perfluoroheptadecyl group, a perchloroheptadecyl group, a perbromoheptadecyl group, a perfluorooctadecyl group, a perchlorooctadecyl group and a perbromooctadecyl group etc.

The preferable specific example of sulfonic acids represented by the general formula [4] includes alkylsulfonic acids such as, for example, a methanesulfonic acid, ethanesulfonic acid, propanesulfonic acid, butanesulfonic acid, pentanesulfonic acid, hexanesulfonic acid, heptanesulfonic acid, octanesulfonic acid, nonanesulfonic acid, decanesulfonic acid, undecanesulfonic acid, dodecanesulfonic acid, tridecanesulfonic acid, tetradecanesulfonic acid, pentadecanesulfonic acid, hexadecanesulfonic acid, heptadecanesulfonic acid and octadecanesulfonic acid; haloalkylsulfonic acids such as, for example, fluorometanesulfonic acid, difluorometanesulfonic acid, trifluorometanesulfonic acid, chlorometanesulfonic acid, dichlorometanesulfonic acid, trichlorometanesulfonic acid, bromometanesulfonic acid, dibromometanesulfonic acid, tribromometanesulfonic acid, iodometanesulfonic acid, diiodometanesulfonic acid, triiodometanesulfonic acid, fluoroetanesulfonic acid, difluoroetanesulfonic acid, trifluoroetanesulfonic acid, pentafluoroethanesulfonic acid, chloroethanesulfonic acid, dichloroethanesulfonic acid, trichloroethanesulfonic acid, pentachloroethanesulfonic acid, tribromoethanesulfonic acid, pentabromoethanesulfonic acid, triiodoethanesulfonic acid, pentaiodoethanesulfonic acid, fluoropropanesulfonic acid, trifluoropropanesulfonic acid, heptafluoropropanesulfonic acid, chloropropanesulfonic acid, trichloropropanesulfonic acid, heptachloropropanesulfonic acid, bromopropanesulfonic acid, tribromopropanesulfonic acid, heptabromopropanesulfonic acid, triiodopropanesulfonic acid, heptaiodopropanesulfonic acid, trifluorobutanesulfonic acid, nonafluorobutanesulfonic acid, trichlorobutanesulfonic acid, nonachlorobutanesulfonic acid, tribromobutanesulfonic acid, nonabromobutanesulfonic acid, triiodobutanesulfonic acid, nonaiodobutanesulfonic acid, trifluoropentanesulfonic acid, perfluoropentanesulfonic acid, trichloropentanesulfonic acid, perchloropentanesulfonic acid, tribromopentanesulfonic acid, perbromopentanesulfonic acid, triiodopentanesulfonic acid, periodopentanesulfonic acid, trifluorohexanesulfonic acid, perfluorohexanesulfonic acid, trichlorohexanesulfonic acid, perchlorohexanesulfonic acid, perbromohexanesulfonic acid, periodohexanesulfonic acid, trifluoroheptanesulfonic acid, perfluoroheptanesulfonic acid, trichloroheptanesulfonic acid, perchloroheptanesulfonic acid, perbromoheptanesulfonic acid, periodoheptanesulfonic acid, trifluorooctanesulfonic acid, perfluorooctanesulfonic acid, trichlorooctanesulfonic acid, perchlorooctanesulfonic acid, perbromooctanesulfonic acid, periodooctanesulfonic acid, trifluorononanesulfonic acid, perfluorononanesulfonic acid, trichlorononanesulfonic acid, perchlorononanesulfonic acid, perbromononanesulfonic acid, periodononanesulfonic acid, trifluorodecanesulfonic acid, perfluorodecanesulfonic acid, trichlorodecanesulfonic acid, perchlorodecanesulfonic acid, perbromodecanesulfonic acid, periododecanesulfonic acid, trifluoroundecanesulfonic acid, perfluoroundecanesulfonic acid, trichloroundecanesulfonic acid, perchloroundecanesulfonic acid, perbromoundecanesulfonic acid, periodoundecanesulfonic acid, trifluorododecanesulfonic acid, perfluorododecanesulfonic acid, trichlorododecanesulfonic acid, perchlorododecanesulfonic acid, perbromododecanesulfonic acid, periodododecanesulfonic acid, trifluorotridecanesulfonic acid, perfluorotridecanesulfonic acid, trichlorotridecanesulfonic acid, perchlorotridecanesulfonic acid, perbromotridecanesulfonic acid, periodotridecanesulfonic acid, trifluorotetradecanesulfonic acid, perfluorotetradecanesulfonic acid, trichlorotetradecanesulfonic acid, perchlorotetradecanesulfonic acid, perbromotetradecanesulfonic acid, periodotetradecanesulfonic acid, trifluoropentadecanesulfonic acid, perfluoropentadecanesulfonic acid, trichloropentadecanesulfonic acid, perchloropentadecanesulfonic acid, perbromopentadecanesulfonic acid, periodopentadecanesulfonic acid, perfluorohexadecanesulfonic acid, perchlorohexadecanesulfonic acid, perbromohexadecanesulfonic acid, periodohexadecanesulfonic acid, perfluoroheptadecanesulfonic acid, perchloroheptadecanesulfonic acid, perbromoheptadecanesulfonic acid, periodoheptadecanesulfonic acid, perfluorooctadecanesulfonic acid, perchlorooctadecanesulfonic acid, perbromooctadecanesulfonic acid and periodooctadecanesulfonic acid; cycloalkylsulfonic acids such as, for example, cyclopentanesulfonic acid and cyclohexanesulfonic acid; halogenated cycloalkylsulfonic acids such as, for example, 2-fluorocyclopentanesulfonic acid, 2-chlorocyclopentanesulfonic acid, 2-bromocyclopentanesulfonic acid, 2-iodocyclopentanesulfonic acid, 3-fluorocyclopentanesulfonic acid, 3-chlorocyclopentanesulfonic acid, 3-bromocyclopentanesulfonic acid, 3-iodocyclopentanesulfonic acid, 3,4-difluorocyclopentanesulfonic acid, 3,4-dichlorocyclopentanesulfonic acid, 3,4-dibromocyclopentanesulfonic acid, 3,4-diiodocyclopentanesulfonic acid, 4-fluorocyclohexanesulfonic acid, 4-chlorocyclohexanesulfonic acid, 4-bromocyclohexanesulfonic acid, 4-iodocyclohexanesulfonic acid, 2,4-difluorocyclohexanesulfonic acid, 2,4-dichlorocyclohexanesulfonic acid, 2,4-dibromocyclohexanesulfonic acid, 2,4-diiodocyclohexanesulfonic acid, 2,4,6-trifluorocyclohexanesulfonic acid, 2,4,6-trichlorocyclohexanesulfonic acid, 2,4,6-tribromocyclohexanesulfonic acid, 2,4,6-triiodocyclohexanesulfonic acid, tetrafluorocyclohexanesulfonic acid, tetrachlorocyclohexanesulfonic acid, tetrabromocyclohexanesulfonic acid and tetraiodocyclohexanesulfonic acid; aromatic sulfonic acids such as, for example, benzenesulfonic acid, naphthalenesulfonic acid, anthracenesulfonic acid, phenanthrenesulfonic acid and pyrenesulfonic acid; halogenated aromatic sulfonic acids such as, for example, 2-fluorobenzenesulfonic acid, 3-fluorobenzenesulfonic acid, 4-fluorobenzenesulfonic acid, 2-chlorobenzenesulfonic acid, 3-chlorobenzenesulfonic acid, 4-chlorobenzenesulfonic acid, 2-bromobenzenesulfonic acid, 3-bromobenzenesulfonic acid, 4-bromobenzenesulfonic acid, 2-iodobenzenesulfonic acid, 4-iodobenzenesulfonic acid, 2,4-difluorobenzenesulfonic acid, 2,6-difluorobenzenesulfonic acid, 2,4-dichlorobenzenesulfonic acid, 2,6-dichlorobenzenesulfonic acid, 2,4-dibromobenzenesulfonic acid, 2,6-dibromobenzenesulfonic acid, 2,4-diiodobenzenesulfonic acid, 2,6-diiodobenzenesulfonic acid, 2,4,6-trifluorobenzenesulfonic acid, 3,4,5-trifluorobenzenesulfonic acid, 2,4,6-trichlorobenzenesulfonic acid, 3,4,5-trichlorobenzenesulfonic acid, 2,4,6-tribromobenzenesulfonic acid, 3,4,5-tribromobenzenesulfonic acid, 2,4,6-triiodobenzenesulfonic acid, 3,4,5-triiodobenzenesulfonic acid, pentafluorobenzenesulfonic acid, pentachlorobenzenesulfonic acid, pentabromobenzenesulfonic acid, pentaiodobenzenesulfonic acid, fluoronaphthalenesulfonic acid, chloronaphthalenesulfonic acid, bromonaphthalenesulfonic acid, iodonaphthalenesulfonic acid, fluoroanthracenesulfonic acid, chloroanthracenesulfonic acid, bromoanthracenesulfonic acid and iodoanthracenesulfonic acid; alkyl substituted aromatic sulfonic acids such as, for example, p-toluenesulfonic acid, 4-isopropylbenzenesulfonic acid, 3,5-bis(trimethyl)benzenesulfonic acid, 3,5-bis(isopropyl)benzenesulfonic acid, 2,4,6-tris(trimethyl)benzenesulfonic acid and 2,4,6-tris(isopropyl)benzenesulfonic acid; halogenated alkyl aromatic sulfonic acids such as, for example, 2-trifluoromethylbenzenesulfonic acid, 2-trichloromethylbenzenesulfonic acid, 2-tribromomethylbenzenesulfonic acid, 2-triiodomethylbenzenesulfonic acid, 3-trifluoromethylbenzenesulfonic acid, 3-trichloromethylbenzenesulfonic acid, 3-tribromomethylbenzenesulfonic acid, 3-triiodomethylbenzenesulfonic acid, 4-trifluoromethylbenzenesulfonic acid, 4-trichloromethylbenzenesulfonic acid, 4-tribromomethylbenzenesulfonic acid, 4-triiodomethylbenzenesulfonic acid, 2,6-bis(trifluoromethyl)benzenesulfonic acid, 2,6-bis(trichloromethyl)benzenesulfonic acid, 2,6-bis(tribromomethyl)benzenesulfonic acid, 2,6-bis(triiodomethyl)benzenesulfonic acid, 3,5-bis(trifluoromethyl)benzenesulfonic acid, 3,5-bis(trichloromethyl)benzenesulfonic acid, 3,5-bis(tribromomethyl)benzenesulfonic acid and 3,5-bis(triiodomethyl)benzenesulfonic acid; aromatic aliphatic sulfonic acids such as, for example, benzylsulfonic acid, phenethylsulfonic acid, phenylpropylsulfonic acid, phenylbutylsulfonic acid, phenylpentylsulfonic acid, phenylhexylsulfonic acid, phenylheptylsulfonic acid, phenyloctylsulfonic acid and phenylnonylsulfonic acid; halogenated aromatic aliphatic sulfonic acids such as, for example, 4-fluorophenylmethylsulfonic acid, 4-chlorophenylmethylsulfonic acid, 4-bromophenylmethylsulfonic acid, 4-iodophenylmethylsulfonic acid, tetrafluorophenylmethylsulfonic acid, tetrachlorophenylmethylsulfonic acid, tetrabromophenylmethylsulfonic acid, tetraiodophenylmethylsulfonic acid, 4-fluorophenylethylsulfonic acid, 4-chlorophenylethylsulfonic acid, 4-bromophenylethylsulfonic acid, 4-iodophenylethylsulfonic acid, 4-fluorophenylpropylsulfonic acid, 4-chlorophenylpropylsulfonic acid, 4-bromophenylpropylsulfonic acid, 4-iodophenylpropylsulfonic acid, 4-fluorophenylbutylsulfonic acid, 4-chlorophenylbutylsulfonic acid, 4-bromophenylbutylsulfonic acid and 4-iodophenylbutylsulfonic acid; and alicyclic sulfonic acids such as, for example, campholsulfonic acid and adamantanesulfonic acid etc.; and among these, fluorine-containing alkylsulfonic acids such as, for example, trifluorometanesulfonic acid and pentafluoroethanesulfonic acid and p-toluenesulfonic acid are preferable.

The involatile acid catalyst includes preferably an acid having strong acidity, more preferably, for example, sulfuric acid and p-toluenesulfonic acid, among the above examples.

The weak basic substance is not particularly limited as long as it does not hydrolyze the ester compound obtained by the method of the present invention, and includes, for example, a weak basic substance having a pKa of usually 4 to 13, preferably 6 to 12, inorganic weak bases such as, for example, specifically a carbonate, a hydrogencarbonate, a phosphate and an acetate, for example, amine compounds represented by the general formula [5]:

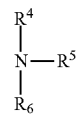

[5]

(wherein $R^4$ to $R^6$ are each independently a hydrogen atom, an alkyl group which may have a substituent, an aryl group and an aralkyl group, and $R^4$ to $R^6$ may form a heterocycle with $R^4$ to $R^6$ and a nitrogen atom binding to them. Provided that at least one of $R^4$ to $R^6$ is an alkyl group, an aryl group or an aralkyl group, or a heterocycle formed with $R^4$ to $R^6$ and a nitrogen atom binding to them); and diamine compounds such as, for example, 1,8-diazabicyclo[5.4.0]undeca-7-ene and 1,4-diazabicyclo[2.2.2]octane (DABCO), etc.

In the general formula [5], the alkyl group of an alkyl group that may have a substituent represented by $R^4$ to $R^6$ includes any of a straight-chained, branched and cyclic group, and usually includes a group having 1 to 18 carbon atoms, preferably 1 to 8 carbon atoms and specifically, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 1-methylpentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a 2-ethylhexyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a n-tridecyl group, an isotridecyl group, a sec-tridecyl group, a tert-tridecyl group, a neotridecyl group, a n-tetradecyl group, an isotetradecyl group, a sec-tetradecyl group, a tert-tetradecyl group, a neotetradecyl group, a n-pentadecyl group, an isopentadecyl group, a sec-pentadecyl group, a tert-pentadecyl group, a neopentadecyl group, a n-hexadecyl group, an isohexadecyl group, a sec-hexadecyl group, a tert-hexadecyl group, a neohexadecyl group, a n-heptadecyl group, an isoheptadecyl group, a sec-heptadecyl group, a tert-heptadecyl group, a neoheptadecyl group, a n-octadecyl group, an isooctadecyl group, a sec-octadecyl group, a tert-octadecyl group, a neooctadecyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, a cyclotridecyl group, a cyclotetradecyl group, a cyclopentadecyl group, a cyclohexadecyl group, a cycloheptadecyl group and a cyclooctadecyl group etc.

The substituent of the alkyl group which may have a substituent includes an alkyl-substituted amino group. The alkyl-substituted amino group includes an amino group of which the hydrogen atom is substituted with an alkyl group having 1 to 3 carbon atoms (for example, a methyl group, an ethyl group, a n-propyl group and an isopropyl group) and specifically, for example, a dimethylamino group, a diethylamino group and a dipropylamino group.

The aryl group represented by $R^4$ to $R^6$ usually includes a group having 6 to 15 carbon atoms and specifically, for example, a phenyl group, a naphthyl group and an anthryl group etc.

The aralkyl group represented by $R^4$ to $R^6$ usually includes a group having 7 to 15 carbon atoms and specifically, for example, a benzyl group, a phenethyl group, a phenylpropyl group and a naphthylmethyl group etc.

The heterocycle formed by $R^4$ to $R^6$ and a nitrogen atom binding to them includes a 5- or 6-membered ring of usually 1 to 4 nitrogen atoms, preferably 1 to 3 nitrogen atoms, specifically heterocyclic aromatic rings such as, for example, a pyridine ring, a pyrrole ring, a pyrroline ring, a quinoline ring, an indole ring, an isoindoline ring and a carbazole ring, and heterocyclic aliphatic rings such as, for example, a pyrrolidine ring, a piperidine ring and a piperazine ring.

The heterocycle may further have an alkyl group having 1 to 3 carbon atoms such as, for example, a methyl group, an ethyl group, a n-propyl group and an isopropyl group and preferably includes specifically, for example, 2,3-lutidine, 2,4-lutidine, 2,5-lutidine, 2,6-lutidine, 3,4-lutidine, 3,5-lutidine, 2,4,6-collidine, α-collidine (4-ethyl-2-methylpyridine), 13-collidine (3-ethyl-4-methylpyridine) and γ-collidine (2,4,6-collidine).

The carbonate as the weak inorganic bases preferably includes specifically alkaline metal carbonates such as, for example, lithium carbonate, sodium carbonate and potassium carbonate, and alkaline-earth metal carbonates such as, for example, magnesium carbonate, calcium carbonate and barium carbonate, and more preferably includes, for example, sodium carbonate and potassium carbonate among these.

The hydrogencarbonate preferably includes specifically alkaline metal hydrogencarbonates such as, for example, sodium hydrogencarbonate and potassium hydrogencarbonate and more preferably includes sodium hydrogencarbonate among these.

The phosphate preferably includes specifically, for example, tertiary sodium phosphate and tertiary potassium phosphate etc.

The acetate preferably includes specifically, for example, sodium acetate and potassium acetate etc.

The amine compound represented by the general formula [5] preferably includes specifically primary amines such as, for example, methylamine, ethylamine, n-propylamine, isopropylamine, n-butylamine, isobutylamine, sec-butylamine, tert-butylamine, pentylamine, isopentylamine, sec-pentylamine, tert-pentylamine, neopentylamine, hexylamine, isohexylamine, sec-hexylamine, tert-hexylamine, neohexylamine, heptylamine, octylamine, (2-ethylhexyl)amine, decylamine, cetylamine, cyclopropylamine, cyclobutylamine, cyclopentylamine and cyclohexylamine; secondary amines such as, for example, secondary alkylamines including for example, dimethylamine, diethylamine, di-n-propylamine, diisopropylamine, di-n-butylamine, diisobutylamine, di-sec-butylamine, di-tert-butylamine, di-n-pentylamine, diisopentylamine, di-sec-pentylamine, di-tert-pentylamine, dineopentylamine, dihexylamine, diisohexylamine, di-sec-hexylamine, di-tert-hexylamine, dineohexylamine, diheptylamine, dioctylamine, bis(2-ethylhexyl)amine, didecylamine, dicetylamine, dicyclopropylamine, dicyclobutylamine, dicyclopentylamine, dicyclohexylamine, methylethylamine and isopropylethylamine; secondary arylamines including for example, diphenylamine and dinaphthylamine; secondary aralkylamines such as, for example, dibenzylamine; and secondary cyclic amines including for example, piperidine, pyrrolidine and piperazine; tertiary amines such as, for example, tertiary alkylamines including for example, trimethylamine, triethylamine, tri-n-propylamine, triisopropylamine, tri-n-butylamine, triisobutylamine, tri-sec-butylamine, tri-tert-butylamine, tri-n-pentylamine, triisopentylamine, tri-sec-pentylamine, tri-tert-pentylamine, trineopentylamine, trihexylamine, triisohexylamine, tri-sec-hexylamine, tri-tert-hexylamine, trineohexylamine, tricyclopropylamine, tricyclobutylamine, tricyclopentylamine amine, tricyclohexylamine, dimethylethylamine and diisopropylethylamine; tertiary arylamines including for example, triphenylamine and trinaphthylamine; tertiary aralkylamines including for example, tribenzylamine; and tertiary cyclic amines including for example, pyridine, 2,3-lutidine, 2,4-lutidine, 2,5-lutidine, 2,6-lutidine, 3,4-lutidine, 3,5-lutidine, 2,4,6-collidine, α-collidine (4-ethyl-2-methylpyridine), β-collidine (3-ethyl-4-methylpyridine) and γ-collidine (2,4,6-collidine); and, for example, tetramethylethylenediamine.

Even a weak basic substance that is hardly soluble in the reaction solution related to the present invention can form a salt with an acid catalyst. Considering, for example, treatment time and treatment temperature, however, a weak basic substance that is soluble in the reaction solution is preferable because it can efficiently form a salt with an acid catalyst. Organic bases such as, for example, triethylamine and pyridine are more preferable as the weak basic substance.

The nonaqueous solvent to be used in the present invention includes a solvent that forms an azeotrope with water and is soluble in the ester compound represented by the general formula [3], obtained by the present invention has not high solubility to a salt (neutralized salt) formed from an involatile acid catalyst and a weak basic substance, and for example, a nonprotonic polar solvent or a nonpolar solvent. The nonprotonic polar solvent includes ethers such as, for example, diethyl ether, diisopropyl ether, tetrahydrofuran and 1,4-dioxane; halogenated hydrocarbons such as, for example, methyl chloride, dichloromethane and chloroform; ketones such as, for example, acetone, methyl ethyl ketone and methyl isobutyl ketone; amides such as, for example, N,N-dimethylformamide, dimethylacetoamide and N-methylpyrrolidone; nitriles such as, for example, acetonitrile, propionitrile and butyronitrile; and dimethyl sulfoxide. Dichlorometane is preferable among these. The nonpolar solvent includes aliphatic hydrocarbons such as, for example, pentane, n-hexane, cyclohexane, heptane and petroleum ether; and aromatic hydrocarbons such as, for example, benzene, toluene and xylene. Toluene or xylene is preferable among these. These solvents may be used alone or in combination of two or more solvents.

The method for producing an ester compound of the present invention is described in detail as follows.

That is, for example, an alcohol represented by the general formula [1] and a carboxylic acid represented by the general formula [2] are reacted (esterification) without any solvent or in a nonaqueous solvent in the presence of an acid catalyst, and dehydrated if necessary, and then a weak basic substance is added to the obtained reaction solution to form a salt with the acid catalyst (neutralization) and the salt is removed. The reaction solution is subjected to purification treatment such as distillation if necessary to obtain an objective ester compound represented by the general formula [3].

While the esterification related to the present invention proceeds without a reaction solvent, it is preferable to carry out the present invention in the coexistence of a nonaqueous solvent because of better reaction efficiency and easier handling in neutralization of an acid catalyst.

The amount of an alcohol represented by the general formula [1] to be used in the production method of the present invention is usually 0.5 to 50 times by mole, preferably 0.5 to 20 times by mole and more preferably 0.8 to 5 times by mole relative to the carboxylic acid, which is a raw material, represented by the general formula [2], although it depends on the kind and amount of the carboxylic acid or an acid catalyst, or whether a reaction solvent is present or not.

When the carboxylic acid to be used in the production method of the present invention is a dicarboxylic acid represented by the general formula [12], the amount of the alcohol is usually 1 to 100 times by mole, preferably 1 to 40 times by mole and more preferably 1.6 to 10 times by mole relative to the dicarboxylic acid, which is a raw material, although it depends on the kind and amount of the dicarboxylic acid or an acid catalyst, or whether a reaction solvent is present or not.

When the alcohol to be used in the production method of the present invention is an alcohol represented by the general formula [9], the amount of the alcohol is usually 0.25 to 25 times by mole, preferably 0.25 to 10 times by mole and more preferably 0.4 to 2.5 times by mole relative to the carboxylic acid, which is a raw material, represented by the general formula [2], although it depends on the kind and amount of the carboxylic acid or an acid catalyst, or whether a reaction solvent is present or not.

The amount of the acid catalyst to be used is usually 0.001 to 1.0 times by mole, preferably 0.01 to 0.8 times by mole and more preferably 0.1 to 0.5 times by mole relative to the said alcohol or a compound represented by the general formula [7] when the raw material is the said compound, although it depends on the kind and amount of the alcohol and a carboxylic acid, or whether a reaction solvent is present or not.

The time of heating (refluxing) in esterification is usually 30 minutes to 50 hours, preferably 3 to 10 hours.

The temperature of heating (refluxing) is usually 30 to 300° C., preferably 30 to 150° C.

Heating (refluxing) is preferably carried out under an atmosphere of an inert gas such as argon and nitrogen.

When the alcohol or/and carboxylic acid as a substance is substitutable as a reaction solvent, the esterification reaction related to the present invention may be carried out without any other solvent.

Dehydration is attained by removing the water formed as a by-product in the esterification of the present invention from the reaction solution and specifically, carried out, for example, by adding a nonaqueous solvent to form an azeotrope with water to the reaction solution and then removing the formed azeotrope from the reaction solution (reflux dehydration treatment). The reflux dehydration treatment may be carried out, separately from the esterification, but preferably is carried out simultaneously with reflux heating in the esterification because the objective ester compound can be efficiently produced by removing water formed as by-product during the esterification.

Esterification using no solvent is carried out by reflux heating in the coexistence of a dehydrating agent to be usually used in a reaction system in this field (adsorption dehydration treatment). The dehydration agent includes an agent to be usually used in this field such as molecular sieve.

Such proper dehydration gives an advantage of easy treatment and increased efficiency because the water formed as by-product in esterification can be removed from the reaction system before neutralization leading to no liquid separation such as extraction.

When the alcohol or carboxylic acid related to the present invention has a polymerizable double bond in the molecule (that is, when $R^1$ or/and $R^2$ in the general formulae [1] and [2] is an alkenyl group), a polymerization inhibitor is preferably added to the reaction system in order to prevent polymerization of the alcohol or/and carboxylic acid and the obtained ester compound.

The polymerization inhibitor is not particularly limited as long as it can prevent polymerization of a raw material alcohol or/and carboxylic acid and a product ester compound, and includes specifically, for example, hydroquinones such as hydroquinone and methyl hydroquinone; tert-butyl catechol, 2,6-di-tert-butyl-4-methylphenol (BHT), phenothiazine, tri-p-nitrophenylmethyl, di-p-fluorophenylamine, diphenylpicrylhydrazyl, N-(3-N-oxyanilino-1,3-dimethylbutylidene) aniline oxide, benzoquinone, methoquinone, nitrosobenzene, picric acid, dithiobenzoyldisulfide, cupferron, copper chloride (II) and p-methoxyphenol etc. For example, tert-butyl catechol, hydroquinone, 2,6-di-tert-butyl-4-methylphenol (BHT), methyl hydroquinone and phenothiazine are preferable among these. These inhibitors may be used alone or in combination of two or more as appropriate.

A too small amount of a polymerization inhibitor can not effectively prevent polymerization, while its too large amount causes a quality and functional problem that an increased amount of the polymerization inhibitor remains in for example, ester compound as the product. The amount of a polymerization inhibitor, therefore, is usually 0.0001 to 10% by weight, preferably 0.005 to 1.0% by weight relative to the total amount of the alcohol and carboxylic acid as raw materials.

A too small amount of a weak basic substance does not sufficiently neutralize an acid catalyst causing the acid catalyst to remain in the ester compound as impurities, while its too large amount causes an increased amount of the weak basic substance to remain in the reaction system. The amount of a weak basic substance, therefore, is usually 1 to 3 times by mole, preferably 1.5 to 2 times by mole relative to the said acid catalyst to be used.

The temperature of neutralization is usually −50 to 150° C., preferably 0 to 50° C.

The time of neutralization is usually 0.5 to 10 hours, preferably 0.5 to 2 hours.

A neutralized salt generated by neutralization, that is, a salt formed from an acid catalyst and a weak basic substance may be removed as appropriately from the reaction solution by, for example, filtration (adsorption) and liquid separation, the treatment method may be selected as appropriately according to the state (for example, solid, oil, liquid) of a neutralized salt.

A filter aid may be added to a reaction solution when a neutralized salt is removed from the reaction solution by filtration.

The filter aid to be used for filtration includes, for example, diatomaceous earth, silica gel, activated carbon, hydroxyapatite, alumina and alumina silica.

The amount of an adsorbent to be used is usually 0.001 to 10 times by mole, preferably 0.01 to 1 times by mole relative to the said ester compound represented by the general formula [3].

For example, instead of the weak basic substance related to the present invention, a weak basic ion-exchange resin and a polymer having a weak basic group may be used. When these materials are used as a weak base, they are also able to serve as a filtration aid in neutralization of an acid catalyst in the reaction solution.

Any weak basic ion-exchange resin may be used as long as it has not an adverse effect on the esterification of the present invention, the weak basic ion-exchange resin includes, for example, an ion-exchange resin wherein a polymer crosslinked by a bifunctional monomer is contained as the skeleton polymer to which weak basic groups are bonded and the weak basic groups are exchanged each with various anions (counter ions), and specifically, for example, a styrene-divinylbenzene copolymer of which the aromatic ring is bonded with an amino group. The amino group includes every group derived from the amino compound represented by the general formula [5] as the above basic substance.

The polymer having a weak basic group is not particularly limited as long as it has not an adverse effect on the esterification of the present invention and includes a polymer having a weak basic group, for example, a polymer having a weak basic group derived from the amino compound represented by the general formula [5].

The base polymer of the polymer having a weak basic group includes, for example, a polymer or copolymer of a monomer represented by the general formula [6]:

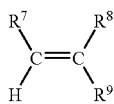

[6]

(wherein $R^7$ represents a hydrogen atom, a lower alkyl group, a carboxyl group, a carboxyalkyl group, an alkyloxycarbonyl group, a hydroxyalkyloxycarbonyl group, a cyano group or a folmyl group; $R^8$ represents a hydrogen atom, a lower alkyl group, a carboxyl group, an alkyloxycarbonyl group, a hydroxyalkyloxycarbonyl group, a cyano group or a halogen atom; $R^9$ represents a hydrogen atom, a lower alkyl group, a haloalkyl group, a hydroxyl group, an aryl group which may have a substituent, an aliphatic heterocyclic group, an aromatic heterocyclic group, a halogen atom, an alkyloxycarbonyl group, a hydroxyalkyloxycarbonyl group, a sulfo group, a cyano group, a cyano-containing alkyl group, an acyloxy group, a carboxyl group, a carboxyalkyl group, an aldehyde group, an amino group, an aminoalkyl group, a carbamoyl group, a N-alkylcarbamoyl group or a hydroxyalkyl group, and $R^7$ and $R^8$ may combine and form an aliphatic ring with an adjacent —C=C—.)

In the general formula [6], the lower alkyl group represented by $R^7$ to $R^9$ may be any of a straight-chained, branched and cyclic group and includes, for example, an alkyl group having 1 to 6 carbon atoms and specifically a methyl group, an ethyl group, a n-propyl group, an isopropyl group, a n-butyl group, an isobutyl group, a tert-butyl group, a sec-butyl group, a n-pentyl group, an isopentyl group, a tert-pentyl group, a 1-methylpentyl group, a n-hexyl group, an isohexyl group, a cyclopropyl group, a cyclopentyl group and a cyclohexyl group etc.

The carboxyalkyl group represented by $R^7$ and $R^9$ includes, for example, a group formed by substituting a part of hydrogen atoms of the above lower alkyl group with a carboxyl group and specifically, for example, a carboxymethyl group, a carboxyethyl group, a carboxypropyl group, a carboxybutyl group, a carboxypentyl group and a carboxyhexyl group etc.

The alkyloxycarbonyl group represented by $R^7$ to $R^9$ includes, for example, a group having preferably 2 to 11 carbon atoms and specifically, for example, a methoxycarbonyl group, an ethoxycarbonyl group, a propoxycarbonyl group, a butoxycarbonyl group, a pentyloxycarbonyl group, a hexyloxycarbonyl group, a heptyloxycarbonyl group, a 2-ethylhexyloxycarbonyl group, an octyloxycarbonyl group, a nonyloxycarbonyl group and a decyloxycarbonyl group etc.

The hydroxyalkyloxycarbonyl group represented by $R^7$ to $R^9$ includes, for example, a group formed by substituting a part of hydrogen atoms of the above alkyloxycarbonyl group having 2 to 11 carbon atoms with a hydroxyl group and specifically, for example, a hydroxymethyloxycarbonyl group, a hydroxyethyloxycarbonyl group, a hydroxypropyloxycarbonyl group, a hydroxybutyloxycarbonyl group, a hydroxypentyloxycarbonyl group, a hydroxyhexyloxycarbonyl group, a hydroxyheptyloxycarbonyl group, a hydroxyoctyloxycarbonyl group, a hydroxynonyloxycarbonyl group and a hydroxydecyloxycarbonyl group etc.

The halogen atom represented by $R^8$ and $R^9$ includes, for example, a fluorine atom, a chlorine atome, a bromine atome and an iodine atom.

The haloalkyl group represented by $R^9$ includes, for example, a group formed by halogenation (for example, fluorination, chlorination, bromination and iodination) of the above lower alkyl group having 1 to 6 carbon atoms, represented by $R^7$ to $R^9$ and specifically, for example, a chloromethyl group, a bromomethyl group, a trifluoromethyl group, a 2-chloroethyl group, a 3-chloropropyl group, a 3-bromopropyl group, a 3,3,3-trifluoropropyl group, a 4-chlorobutyl group, a 5-chloropentyl group and a 6-chlorohexyl group etc.

The aryl group of an aryl group which may have a substituent includes, for example, a phenyl group, a tolyl group, a xylyl group and a naphthyl group, and the said substituent includes, for example, an amino group, a hydroxyl group, a lower alkoxy group and a carboxyl group. The substituted aryl group includes specifically, for example, an aminophenyl group, toluidino group, hydroxyphenyl group, methoxyphenyl group, tert-butoxyphenyl group and carboxyphenyl group.

The aliphatic heterocyclic group includes preferably a 5-membered or 6-membered ring having 1 to 3 hetero atoms such as, for example, a nitrogen atom, oxygen atom and sulfur atom and specifically, for example, a 2-oxopyrrolidyl group, a piperidyl group, a piperidino group, a piperazinyl group and a morpholino group etc.

The aromatic heterocyclic group includes preferably a 5-membered or 6-membered ring having 1 to 3 hetero atoms such as, for example, a nitrogen atom, an oxygen atom and a sulfur atom and specifically, for example, a pyridyl group, an imidazolyl group, a thiazolyl group, a furyl group and a pyranyl group.

The cyano-containing alkyl group includes, for example, a group formed by substituting a part of hydrogen atoms of the above lower alkyl group with a cyano group and specifically, for example, a cyanomethyl group, a 2-cyanoethyl group, a 2-cyanopropyl group, a 3-cyanopropyl group, a 2-cyanobutyl group, a 4-cyanobutyl group, a 5-cyanopentyl group and a 6-cyanohexyl group.

The acyloxy group includes, for example, a group derived from a carboxylic acid having 2 to 20 carbon atoms and specifically, for example, an acetyloxy group, propionyloxy group, butyryloxy group, pentanoyloxy group, nonanoyloxy group, decanoyloxy group and benzoyloxy group.

The aminoalkyl group includes a group formed by substituting a part of hydrogen atoms of the above lower alkyl group with an amino group and specifically, for example, an aminomethyl group, an aminoethyl group, an aminopropyl group, an aminobutyl group, an aminopentyl group and an aminohexyl group etc.

The N-alkylcarbamoyl group includes a group formed by substituting a part of hydrogen atoms of a carbamoyl group with an alkyl group and specifically, for example, an N-methylcarbamoyl group, a N-ethylcarbamoyl group, a N-n-propylcarbamoyl group, a N-isopropylcarbamoyl group, a N-n-butylcarbamoyl group and a N-t-butylcarbamoyl group.

The hydroxyalkyl group includes a group formed by substituting a part of hydrogen atoms of the above lower alkyl group with a hydroxyl group and specifically, for example, a hydroxymethyl group, a hydroxyethyl group, a hydroxypropyl group, a hydroxybutyl group, a hydroxypentyl group and a hydroxyhexyl group.

The aliphatic ring of an aliphatic ring formed by combining $R^7$ and $R^8$ with an adjacent —C=C— includes, for example, an unsaturated aliphatic ring having 5 to 10 carbon atoms that may be either monocyclic or polycyclic and specifically, for example, a norbornene ring, a cyclopentene ring, a cyclohexene ring, a cyclooctene ring and a cyclodecene ring.

The monomer represented by the general formula [6] includes specifically ethylenically unsaturated aliphatic hydrocarbons having 2 to 20 carbon atoms such as, for example, ethylene, propylene, butylene and isobutylene; ethylenically unsaturated aromatic hydrocarbons having 8 to 20 carbon atoms such as, for example, styrene, 4-methylstyrene, 4-ethylstyrene and divinylbenzene; alkenyl esters having 3 to 20 carbon atoms such as, for example, vinyl formate, vinyl acetate, vinyl propionate and isopropenyl acetate; halogen-containing ethylenically unsaturated compounds having 2 to 20 carbon atoms such as, for example, vinyl chloride, vinylidene chloride, vinylidene fluoride and tetrafluoroethylene; ethylenically unsaturated carboxylic acids having 3 to 20 carbon atoms (these acids may be a salt such as a salt of an alkaline metal such as sodium and potassium, and an ammonium salt) such as, for example, acrylic acid, methacrylic acid, itaconic acid, maleic acid, fumaric acid, crotonic acid, vinylacetic acid, allylacetic acid and vinylbenzoic acid; ethylenically unsaturated carboxylic esters such as, for example, methyl methacrylate, ethyl methacrylate, propyl methacrylate, butyl methacrylate, 2-ethylhexyl methacrylate, methyl acrylate, ethyl acrylate, propyl acrylate, butyl acrylate, 2-ethylhexyl acrylate, lauryl methacrylate, stearyl acrylate, methyl itaconate, ethyl itaconate, methyl maleate, ethyl maleate, methyl fumarate, ethyl fumarate, methyl crotonate, ethyl crotonate and methyl 3-butenate; cyano-containing ethylenically unsaturated compounds having 3 to 20 carbon atoms such as, for example, acrylonitrile, methacrylonitrile and allyl cyanide; ethylenically unsaturated amide compounds having 3 to 20 carbon atoms such as acrylamide and methacrylamide; ethylenically unsaturated aldehydes having 3 to 20 carbon atoms such as acrolein and crotonaldehyde; ethylenically unsaturated sulfonic acids having 2 to 20 carbon atoms (these acids may be a salt such as a salt of an alkaline metal such as sodium and potassium) such as vinylsulfonic acid and 4-vinylbenzenesulfonic acid; ethylenically unsaturated aliphatic amines having 2 to 20 carbon atoms such as vinylamine and allylamine; ethylenically unsaturated aromatic amines having 8 to 20 carbon atoms such as vinylaniline; ethylenically unsaturated aliphatic heterocyclic amines having 5 to 20 carbon atoms such as N-vinylpyrrolidone and vinylpiperidine; ethylenically unsaturated alcohols having 3 to 20 carbon atoms such as allyl alcohol and crotyl alcohol; and ethylenically unsaturated phenols having 8 to 20 carbon atoms such as 4-vinylphenol.

Introduction of a weak basic group derived from, for example, an amino compound represented by the general formula [5] to these base polymers may be carried out as appropriately according to a known method.

An objective ester compound may be purified as appropriately according to a known purification method such as distillation and crystallization. The treatment after the reaction may be carried out according to an ordinary method of aftertreatment in this field.

The method for producing an ester compound of the present invention can efficiently produce an ester compound without having the problem of conventional methods that a large amount of waste water generated by neutralization of an acid catalyst with water is harmful in view of economy and environment because an acid catalyst is neutralized by a weak basic substance to form a neutralized salt, which is removed from the reaction solution.

Conventional methods which use water for neutralization have a problem of low efficiency in synthesizing a water-soluble ester compound, whereas the production method of the present invention which does not use water for neutralization can efficiently produce a water-soluble ester compound.

Additionally, when water is removed before neutralization, treatment such as liquid separation and washing is not necessary, which makes treatment steps less and improved efficiency possible.

The present invention is described more specifically with reference to the following examples, to which, however, the invention is not limited at all.

EXAMPLES

Example 1

Synthesis of
3,3,4,4,5,5,6,6,7,7,8,8,8-tridecafluorooctane
2-methyl-2-propenic acid ester Toluene (2 L), 3,3,4,4,5,5,6,6,7,7,8,8,8-tridecafluorooctane-1-ol (2.18 kg, 6.0 mol), 2-methyl-2-propenic acid (methacrylic acid) (567 g, 6.6 mol) and 1,4-dihydroxybenzene (hydroquinone) (6.59 g, 60 mmol) were added and then p-toluenesulfonic acid monohydrate (148.06 g, 0.78 mol) was added thereto. The obtained solution was heated and subjected to reflux dehydration at 115° C. for 5 hours. After reflux dehydration, the obtained reaction solution was cooled to around room temperature and added with triethylamine (151.5 g, 1.50 mol) was added thereto, stirred for 0.5 hours and then added with 150 g of silica gel. After stirring for 0.5 hours, the silica gel was filtered off and the obtained filtrate was added with 1,4-dihydroxybenzene (hydroquinone) (1.32 g, 12.0 mmol), and the solvent was removed in vacuum distillation and then was purified in distillation to obtain 3,3,4,4,5,5,6,6,7,7,8,8,8-tridecafluorooctane 2-methyl-2-propenic acid ester (2.44 kg, 94%).

Example 2

Synthesis of Ethyl Methylthioacetate

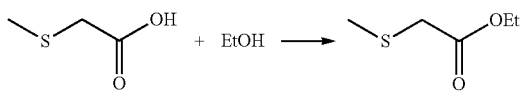

Toluene (30 ml), ethanol (2.39 g, 169.59 mmol) and methylthioacetic acid (15 g, 141.32 mmol) were added into a 100-ml flask in this order at room temperature and then p-toluenesulfonic acid monohydrate (4.03 g, 21.20 mmol) was charged thereto. The solution was gently heated and subjected to reflux dehydration for 3 to 5 hours. After reflux dehydration, the solution was cooled to around room temperature, added with triethylamine (2.86 g, 28.26 mmol) at room temperature, stirred and then added with silica gel. After stirring for a while, the silica gel was filtered off. After the solvent of the filtrate was removed in vacuum distillation, ethyl methylthioacetate (14.81 g, 78%) was isolated in distillation.

Example 3

Synthesis of Ethyl Methoxyacetate

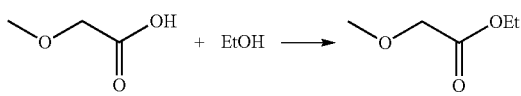

Toluene (100 ml), ethanol (15.34 g, 333.64 mmol) and methoxyacetic acid (25 g, 277.53 mmol) were added into a 200-ml flask in this order at room temperature and then p-toluenesulfonic acid monohydrate (7.92 g, 41.63 mmol) was charged thereto. The solution was gently heated and subjected to reflux dehydration for 3 to 5 hours. After reflux dehydration, the solution was cooled to around room temperature, added with triethylamine (7.02 g, 69.38 mmol) at room temperature, stirred and then added with silica gel. After stirring for a while, the silica gel was filtered off. After the solvent of the filtrate was removed in vacuum distillation, ethyl methoxyacetate (22.21 g, 68%) was isolated in distillation.

Example 4

Synthesis of ethyl p-tolylacetate

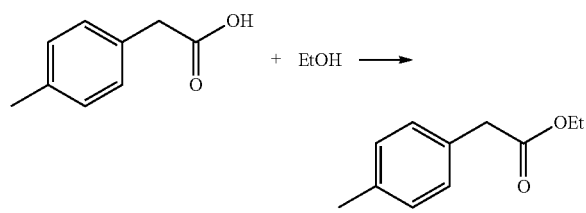

Toluene (100 ml), ethanol (9.20 g, 199.77 mmol) and p-tolylacetic acid (25 g, 166.48 mmol) was added into a 200-ml flask in this order at room temperature and then p-toluenesulfonic acid monohydrate (4.75 g, 24.97 mmol) was charged thereto. The solution was gently heated and subjected to reflux dehydration for 3 to 5 hours. After reflux dehydration, the solution was cooled to around room temperature, added with triethylamine (4.21 g, 41.62 mmol) at room temperature, stirred and then added with silica gel. After stirring for a while, the silica gel was filtered off. After the solvent of the filtrate was removed in vacuum distillation, ethyl p-tolylacetate (28.09 g, 95%) was isolated in distillation.

Example 5

Synthesis of ethyl 2-furancarboxylate

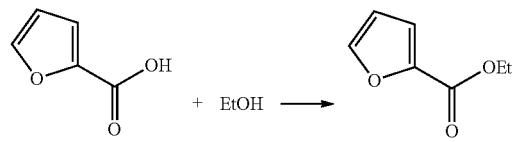 [SMILES: "EtOH" ; O=C(O)c1ccco1 ; CCOC(=O)c1ccco1]

Toluene (100 ml), ethanol (12.33 g, 267.67 mmol) and 2-furancarboxylic acid (25 g, 223.05 mmol) were added into a 200-ml flask in this order at room temperature and then p-toluenesulfonic acid monohydrate (6.65 g, 34.96 mmol) was charged thereto. The solution was gently heated and subjected to reflux dehydration for 3 to 5 hours. After reflux dehydration, the solution was cooled to around room temperature, added with triethylamine (5.64 g, 55.76 mmol) at room temperature, stirred and then added with silica gel. After stirring for a while, the silica gel was filtered off. After the solvent of the filtrate was removed in vacuum distillation, ethyl 2-furancarboxylate (27.60 g, 88%) was isolated in distillation.

Example 6

Synthesis of ethyl 5-chlorovalerate

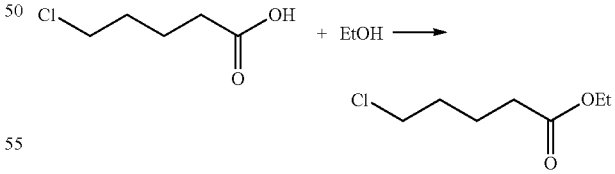

Toluene (100 ml), ethanol (10.12 g, 219.65 mmol) and 5-chlorovaleric acid (25 g, 183.04 mmol) were added into a 200-ml flask in this order at room temperature and then p-toluenesulfonic acid monohydrate (5.22 g, 27.46 mmol) was charged thereto. The solution was gently heated and subjected to reflux dehydration for 3 to 5 hours. After reflux dehydration, the solution was cooled to around room temperature, added with triethylamine (4.63 g, 45.76 mmol) at room temperature, stirred and then added with silica gel. After stirring for a while, the silica gel was filtered off. After the solvent of the filtrate was removed in vacuum distillation, ethyl 5-chlorovalerate (21.54 g, 72%) was isolated in distillation.

Example 7

Synthesis of Ethyl Acetylacetate

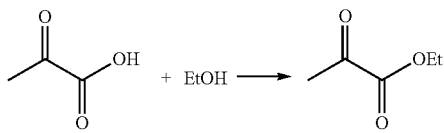

Toluene (100 ml), ethanol (19.86 g, 431.16 mmol) and pivalic acid (31.64 g, 359.30 mmol) were added into a 200-ml flask in this order at room temperature and then p-toluenesulfonic acid monohydrate (10.25 g, 53.90 mmol) was charged thereto. The solution was gently heated and subjected to reflux dehydration for 3 to 5 hours. After reflux dehydration, the solution was cooled to around room temperature, added with triethylamine (9.09 g, 89.83 mmol) at room temperature, stirred and then added with silica gel. After stirring for a while, the silica gel was filtered off. After the solvent of the filtrate was removed in vacuum distillation, ethyl acetylacetate (13.2 g, 32%) was isolated in distillation.

Example 8

Synthesis of Butyl Acetate

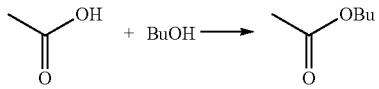

Toluene (100 ml), butanol (7.04 g, 95 mmol) and acetic acid (6.05 g, 100 mmol) were added into a 200-ml flask in this order at room temperature and then p-toluenesulfonic acid monohydrate (2.85 g, 15 mmol) was charged thereto. The solution was gently heated and subjected to reflux dehydration for 3 to 5 hours. After reflux dehydration, the solution was cooled to around room temperature, added with triethylamine (2.40 g, 25 mmol) at room temperature, stirred and then added with silica gel. After stirring for a while, the silica gel was filtered off. After the solvent of the filtrate was removed in vacuum distillation, butyl acetate (9.87 g, 85%) was isolated in distillation.

Example 9

Synthesis of Phenyl Acetate

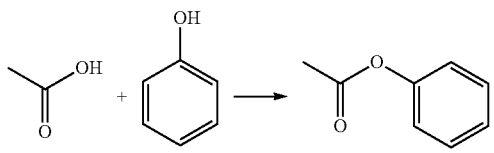

Toluene (100 ml), phenol (8.94 g, 95 mmol) and acetic acid (6.05 g, 100 mmol) were added into a 200-ml flask in this order at room temperature and then p-toluenesulfonic acid monohydrate (2.85 g, 15 mmol) was charged thereto. The solution was gently heated and subjected to reflux dehydration for 3 to 5 hours. After reflux dehydration, the solution was cooled to around room temperature, added with triethylamine (2.40 g, 25 mmol) at room temperature, stirred and then added with silica gel. After continuing to stir for a while, the silica gel was filtered off. After the solvent of the filtrate was removed in vacuum distillation, phenyl acetate (11.64 g, 90%) was isolated in distillation.

The production method of the present invention, which does not use water for neutralization of an acid catalyst, can produce an ester compound efficiently and industrially without the problem of conventional methods that a large amount of waste water is harmful in view of economy and environment.

The invention claimed is:

1. A method for producing an ester compound having a heterocyclic group(s) which comprises:

subjecting a carboxylic acid and an alcohol to a dehydration-condensation reaction with adding no solvent or with adding a nonaqueous solvent into a reaction system, in a presence of an involatile acid catalyst;

then removing a residue of the acid catalyst without adding any solvent or in a nonaqueous solvent by bringing a weak basic substance into contact with the residual acid catalyst, forming a salt of the weak basic substance and the acid catalyst, and then filtering off the salt, wherein the carboxylic acid is a compound represented by a formula (2):

$$R^2\text{—COOH} \tag{2},$$

wherein $R^2$ represents an alkyl group having 1 to 18 carbon atoms, an oxygen-atom-containing alkyl group, an alkenyl group, an alkynyl group, an aryl group, an aralkyl group, or a heterocyclic group, which may have a substituent; and the alcohol is a compound represented by a formula (1):

$$R^1\text{—OH} \tag{1},$$

wherein $R^1$ represents an alkyl group having 1 to 18 carbon atoms, an oxygen-atom-containing alkyl group, an alkenyl group, an alkynyl group, an aryl group, an aralkyl group, or a heterocyclic group, which may have a substituent; and wherein the heterocyclic group represented by $R^1$ and $R^2$ is 5-membered ring or a 6-membered ring, which has 1 to 3 hetero atoms selected from the group consisting of a nitrogen atom, an oxygen atom and a sulfur atom, the substituent of the alkyl group, the alkenyl group, or the alkynyl group represented by $R^1$ and $R^2$ is selected from the group consisting of a halogen atom, a haloalkyl group, an alkoxy group, a haloalkoxy group, a thioalkoxy group, an acyl group, a substituted amino group, a hydroxyl group, a cyano group, a carboxyl group, a nitrile group, and a nitro group, and the substituent of the aryl group, the aralkyl group, or the heterocyclic group represented by $R^1$ and $R^2$ is selected from the group consisting of a halogen atom, an alkyl group, a haloalkyl group, an alkenyl group, an alkoxy group, a haloalkoxy group, a thioalkoxy group, an acyl group, a substituted amino group, a hydroxyl group, a cyano group, a carboxyl group, a nitrile group, and a nitro group; and the ester compound obtained from the above carboxylic acid of the formula (2) and the above alcohol of the formula (1) is a compound represented by a formula (3):

$$R^1\text{—OCO—}R^2 \tag{3}$$

wherein R¹ and R² are same as the above, wherein at least one of R¹ and R² is the heterocyclic group.

2. The method according to claim 1, wherein a dehydration treatment is carried out during the dehydration-condensation reaction.

3. The method according to claim 1, wherein the weak basic substance is
a) an inorganic weak base,
b) an amine compound represented by a formula (5):

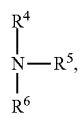

[5]

wherein R⁴ to R⁶ are each independently
a hydrogen atom,
an alkyl group, which may have a substituent, wherein the substituent of the alkyl group is alkyl-substituted amino group, which is an amino group in which the hydrogen atom is substituted with an alkyl group having 1 to 3 carbon atoms,
an aryl group, or an aralkyl group, and
wherein the R⁴ to R⁶ may form a heterocycle group with the R⁴ to R⁶ and a nitrogen atom binding to them, wherein at least one of R⁴ to R⁶ is an alkyl group, an aryl group, or an aralkyl group, or the R⁴ to R⁶ form the heterocycle group with the nitrogen atom binding to them,
c) 1,8-diazabicyclo[5.4.0]undeca-7-ene, or
d) 1,4-diazabicyclo[2.2.2]octane.

4. The method according to claim 1, wherein the weak basic substance is triethylamine or pyridine.

5. The method according to claim 1, wherein the involatile acid catalyst is a sulfuric acid or a sulfonic acid represented by a formula (4):

wherein R³ is an alkyl group, an aryl group, or an aralkyl group, which may have a substituent,
wherein the substituent of the alkyl group, the aryl group, or the aralkyl group is selected from the group consisting of a halogen atom, an alkyl group, and a haloalkyl group.

6. The method according to claim 5, wherein said acid catalyst is sulfuric acid or p-toluenesulfonic acid.

7. The method according to claim 1, wherein the nonaqueous solvent is toluene, dichloromethane or cyclohexane.

8. The method according to claim 1, wherein the filtering treatment is carried out by using a filter aid.

9. The method according to claim 8, wherein the filter aid is diatomaceous earth, silica gel, activated carbon, hydroxyapatite, alumina, or alumina silica.

10. The method according to claim 2, wherein the dehydration treatment is a reflux dehydration treatment.

11. The method according to claim 2, wherein the dehydration treatment is an adsorption dehydration treatment.

12. The method according to claim 1, wherein a polymerization inhibitor further is present in the dehydration-condensation reaction when at least one of R¹ and R² is an alkenyl group or an alkynyl group.

13. The method according to claim 12, wherein the polymerization inhibitor is at least one inhibitor selected from the group consisting of tert-butyl catechol, hydroquinone, 2,6-di-tert-butyl-4-methylphenol, methylhydroquinone, and phenothiazine.

14. A method for producing an ester compound having a heterocyclic group(s), which comprises:
subjecting a carboxylic acid having an alcohol moiety to a dehydration-condensation reaction with adding no solvent or with adding a nonaqueous solvent into a reaction system, in a presence of involatile acid catalyst;
then removing a residue of the acid catalyst without adding any solvent or in a nonaqueous solvent by bringing a weak basic substance into contact with the residual acid catalyst, forming a salt of the weak basic substance and the acid catalyst, and then filtering off the salt,
wherein the carboxylic acid having an alcohol moiety is a compound represented by a formula (7):

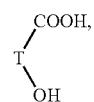

(7)

wherein T is an alkylene chain, which may have a substituent,
wherein the substituent of the alkylene chain is selected from the group consisting of a halogen atom, a haloalkyl group, an alkoxy group, a haloalkoxy group, a thioalkoxy group, an acyl group, a substituted amino group, a hydroxyl group, a cyano group, a carboxyl group, a nitrile group, and a nitro group, and
the ester compound obtained from the above compound of the formula (7) is a compound represented by a formula (8):

(8)

wherein T is same as above.

15. The method according to claim 1, wherein R¹ is the heterocyclic group.

16. The method according to claim 1, wherein R² is the heterocyclic group.

17. The method according to claim 1, wherein the both of R¹ and R² are the heterocyclic group.

18. The method according to claim 1, wherein the heterocyclic group represented by R¹ and R² is a pyrrolidyl-2-one group, a piperidyl group, a piperidino group, a piperazinyl group, a morpholino group, a pyridyl group, an imidazolyl group, a thiazoly group, a furyl group, or a pyranyl group.

19. The method according to claim 14, wherein the weak basic substance is
a) an inorganic weak base,
b) an amine compound represented by a formula (5):

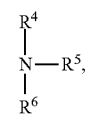

(5)

wherein R⁴ to R⁶ are each independently a hydrogen atom,
an alkyl group, which may have a substituent, wherein the substituent of the alkyl group is alkyl-substituted amino group, which is an amino group in which the hydrogen atom is substituted with an alkyl group having 1 to 3 carbon atoms, an aryl group, or an aralkyl group, and wherein the $R^4$ to $R^6$ may form a heterocycle group with the $R^4$ to $R^6$ and a nitrogen atom binding to them, wherein at least one of $R^4$ to $R^6$ is an alkyl group, an aryl group, or an aralkyl group, or the $R^4$ to $R^6$ form the heterocycle group with the nitrogen atom binding to them, c) 1,8-diazabicyclo[5.4.0]undeca-7-ene, or
d) 1,4-diazabicyclo[2.2.2]octane.

* * * * *